(12) United States Patent
Kapeller-Libermann et al.

(10) Patent No.: US 7,977,059 B2
(45) Date of Patent: Jul. 12, 2011

(54) 17867, A NOVEL HUMAN AMINOPEPTIDASE

(75) Inventors: Rosana Kapeller-Libermann, Chestnut Hill, MA (US); Mark Williamson, Saugus, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 359 days.

(21) Appl. No.: 12/129,509

(22) Filed: May 29, 2008

(65) Prior Publication Data

US 2009/0004672 A1    Jan. 1, 2009

Related U.S. Application Data

(60) Division of application No. 11/333,838, filed on Jan. 17, 2006, now abandoned, which is a division of application No. 10/039,073, filed on Dec. 31, 2001, now Pat. No. 7,034,111, which is a continuation of application No. 09/345,650, filed on Jun. 30, 1999, now Pat. No. 6,362,324.

(51) Int. Cl.
| | |
|---|---|
| *C12Q 1/00* | (2006.01) |
| *G01N 33/00* | (2006.01) |
| *G01N 33/53* | (2006.01) |
| *G01N 33/567* | (2006.01) |
| *G01N 33/573* | (2006.01) |

(52) U.S. Cl. ............ 435/7.1; 435/4; 435/7.21; 435/7.4; 435/7.92

(58) Field of Classification Search ................. None
See application file for complete search history.

(56) References Cited

U.S. PATENT DOCUMENTS
5,972,680 A    10/1999    Knowles

FOREIGN PATENT DOCUMENTS
| EP | 04640533 | 1/1992 |
|---|---|---|
| EP | 0823478 | 2/1998 |
| WO | 9609317 | 3/1996 |
| WO | 9738114 | 10/1997 |
| WO | 9911799 | 3/1999 |
| WO | 9918211 | 4/1999 |

OTHER PUBLICATIONS

Ausubel et al., "Section 1, Expression of Proteins in *Escherichia coli*," Short Protocols in Molecular Biology, second edition, 1992, unit 16.1 and 16.2, pp. 16-4 to 16-9.
Hattori et al., "Molecular Cloning of Adipocyte-Derived Leucine Aminopeptidase Highly Related to Placental Leucine Aminopeptidase/Oxytochinase," J. Biochem. 125, 931-38, May 1999.
Amino Acid and Nucleic Acid Database Report for Accession No. T13311, Jul. 8, 1996.
Amino Acid and Nucleic Acid Database Report for Accession No. A1084822, unpublished, 1997.
Nucleic Acid Database Report for Accession No. V13927, Jul. 20, 1998.
Database Report for Accession No. R94512, Sep. 20, 1994.
Database Report for Accession No. U76997, Direct Submission Oct. 31, 1996.
BLAST Search of Patent, NRP, DBI, DBEST, and NRN Databases, Oct. 21, 1996.
EMBI, Database Report for Accession No. A1248937, Nov. 5, 1998.
EMBI, Database Report for Accession No. AA361076, 1995.

*Primary Examiner* — Alana M Harris
(74) *Attorney, Agent, or Firm* — Banner & Witcoff, Ltd.

(57) ABSTRACT

The present invention relates to a newly identified human aminopeptidase. The invention also relates to polynucleotides encoding the aminopeptidase. The invention further relates to methods using the aminopeptidase polypeptides and polynucleotides as a target for diagnosis and treatment in aminopeptidase-related disorders. The invention further relates to drug-screening methods using the aminopeptidase polypeptides and polynucleotides to identify agonists and antagonists for diagnosis and treatment. The invention further encompasses agonists and antagonists based on the aminopeptidase polypeptides and polynucleotides. The invention further relates to procedures for producing the aminopeptidase polypeptides and polynucleotides.

21 Claims, 10 Drawing Sheets

Input file 17867cons; Output File 17867tra
Sequence length 3366

```
         10        20        30        40        50        60        70
CCCCGCGTCCGGCATGATTTAAGATTAAATTCATGTATTGAAAATATTGTTCAGACCCCATGTGACATAACTGGAGCCA
         80        90       100       110       120       130       140        M   F   H
GTGCAGTGCCATGAAGAACTACGAGATTAGCCTGGATATTAACTTGTCTTCTAGAGAATAGATTTC ATG TTC CAT       154
                                                                   146
  S   S   A   M   V   N   S   H   R   K   P   M   F   N   I   H   R   G   F   Y       23
 TCT TCT GCA ATG GTT AAT TCA CAC AGA AAA CCA ATG TTT AAC ATT CAC AGA GGA TTT TAC      69
  C   L   T   A   I   L   P   Q   I   C   I   C   S   Q   F   S   V   P   S   S       43
 TGC TTA ACA GCC ATC TTG CCC CAA ATA TGC ATT TGT TCT CAG TTC TCA GTG CCA TCT AGT     129
  Y   H   F   T   E   D   P   G   A   F   P   V   A   T   N   G   E   R   F   P       63
 TAT CAC TTC ACT GAG GAT CCT GGG GCT TTC CCA GTA GCC ACT AAT GGG GAA CGA TTT CCT     189
  W   Q   E   L   R   L   P   S   V   V   I   P   L   H   Y   D   L   F   V   H       83
 TGG CAG GAG CTA AGG CTC CCC AGT GTG GTC ATT CCT CTC CAT TAT GAC CTC TTT GTC CAC     249
  P   N   L   T   S   L   D   F   V   A   S   E   K   I   E   V   L   V   S   N      103
 CCC AAT CTC ACC TCT CTG GAC TTT GTT GCA TCT GAG AAG ATC GAA GTC TTG GTC AGC AAT     309
  A   T   Q   F   I   I   L   H   S   K   D   L   E   I   T   N   A   T   L   Q      103
 GCT ACC CAG TTT ATC ATC TTG CAC AGC AAA GAT CTT GAA ATC ACG AAT GCC ACC CTT CAG     369
  S   E   E   D   S   R   Y   M   K   P   G   K   E   L   K   V   L   S   Y   P      143
 TCA GAG GAA GAT TCA AGA TAC ATG AAA CCA GGA AAA GAA CTG AAA GTT TTG AGT TAC CCT     429
  A   H   E   Q   I   A   L   L   V   P   E   K   L   T   P   H   L   K   Y   Y      163
 GCT CAT GAA CAA ATT GCA CTG CTG GTT CCA GAG AAA CTT ACG CCT CAC CTG AAA TAC TAT     489
  V   A   M   D   F   Q   A   K   L   G   D   G   F   E   G   F   Y   K   S   T      183
 GTG GCT ATG GAC TTC CAA GCC AAG TTA GGT GAT GGC TTT GAA GGG TTT TAT AAA AGC ACA     549
  Y   R   T   L   G   G   E   T   R   I   L   A   V   T   D   F   E   P   T   Q      203
 TAC AGA ACT CTT GGT GGT GAA ACA AGA ATT CTT GCA GTA ACA GAT TTT GAG CCA ACC CAG     609
  A   R   M   A   F   P   C   F   D   E   P   L   F   K   A   N   F   S   I   K      223
 GCA CGC ATG GCT TTC CCT TGC TTT GAT GAA CCG TTG TTC AAA GCC AAC TTT TCA ATC AAG     669
  I   R   R   E   S   R   H   I   A   L   S   N   M   P   K   V   K   T   I   E      243
 ATA CGA AGA GAG AGC AGG CAT ATT GCA CTA TCC AAC ATG CCA AAG GTT AAG ACA ATT GAA     729
  L   E   G   G   L   L   E   D   H   F   E   T   T   V   K   M   S   T   Y   L      263
 CTT GAA GGA GGT CTT TTG GAA GAT CAC TTT GAA ACT ACT GTA AAA ATG AGT ACA TAC CTT     789
  V   A   Y   I   V   C   D   F   H   S   L   S   G   F   T   S   S   G   V   K      283
 GTA GCC TAC ATA GTT TGT GAT TTC CAC TCT CTG AGT GGC TTC ACT TCA TCA GGG GTC AAG     849
  V   S   I   Y   A   S   P   D   K   R   N   Q   T   H   Y   A   L   Q   A   S      303
 GTG TCC ATC TAT GCA TCC CCA GAC AAA CGG AAT CAA ACA CAT TAT GCT TTG CAG GCA TCA     909
  L   K   L   L   D   F   Y   E   K   Y   F   D   I   Y   Y   P   L   S   K   L      323
 CTG AAG CTA CTT GAT TTT TAT GAA AAG TAC TTT GAT ATC TAC TAT CCA CTC TCC AAA CTG     969
  D   L   I   A   I   P   D   F   A   P   G   A   M   E   N   W   G   L   I   T      343
 GAT TTA ATT GCT ATT CCT GAC TTT GCA CCT GGA GCC ATG GAA AAT TGG GGC CTC ATT ACA    1029
  Y   R   E   T   S   L   L   F   D   P   K   T   S   S   A   S   D   K   L   W      363
 TAT AGG GAG ACG TCA CTG CTT TTT GAC CCC AAG ACC TCT TCT GCT TCC GAT AAA CTG TGG    1089
  V   T   R   V   I   A   H   E   L   A   H   Q   W   F   G   N   L   V   T   M      383
 GTC ACC AGA GTC ATA GCC CAT GAA CTG GCG CAC CAG TGG TTT GGC AAC CTG GTC ACA ATG    1149
```

FIG. 1A.

```
      E   W   W   N   D   I   W   L   K   E   G   F   A   K   Y   M   E   L   I   A    403
     GAA TGG TGG AAT GAT ATT TGG CTT AAG GAG GGT TTT GCA AAA TAC ATG GAA CTT ATC GCT 1209
      V   N   A   T   Y   P   E   L   Q   F   D   D   Y   F   L   N   V   C   F   E    423
     GTT AAT GCT ACA TAT CCA GAG CTG CAA TTT GAT GAC TAT TTT TTG AAT GTG TGT TTT GAA 1269
      V   I   T   K   D   S   L   N   S   S   R   P   I   S   K   P   A   E   T   P    443
     GTA ATT ACA AAA GAT TCA TTG AAT TCA TCC CGC CCT ATC TCC AAA CCA GCG GAA ACC CCG 1329
      T   Q   I   Q   E   M   F   D   E   V   S   Y   N   K   G   A   C   I   L   N    463
     ACT CAA ATA CAG GAA ATG TTT GAT GAA GTT TCC TAT AAC AAG GGA GCT TGT ATT TTG AAT 1389
      M   L   K   D   F   L   G   E   E   K   F   Q   K   G   I   I   Q   Y   L   K    483
     ATG CTC AAG GAT TTT CTG GGT GAG GAG AAA TTC CAG AAA GGA ATA ATT CAG TAC TTA AAG 1449
      K   F   S   Y   R   N   A   K   N   D   D   L   W   S   S   L   S   N   S   C    503
     AAG TTC AGC TAT AGA AAT GCT AAG AAT GAT GAC TTG TGG AGC AGT CTG TCA AAT AGT TGT 1509
      L   E   S   D   F   T   S   G   G   V   C   H   S   D   P   K   M   T   S   N    523
     TTA GAA AGT GAT TTT ACA TCT GGT GGA GTT TGT CAT TCG GAT CCC AAG ATG ACA AGT AAC 1569
      M   L   A   F   L   G   E   N   A   E   V   K   E   M   M   T   T   W   T   L    543
     ATG CTC GCC TTT CTG GGG GAA AAT GCA GAG GTC AAA GAG ATG ATG ACT ACA TGG ACT CTC 1629
      Q   K   G   I   P   L   L   V   V   K   Q   D   G   C   S   L   R   L   Q   Q    563
     CAG AAA GGA ATC CCC CTG CTG GTG GTT AAA CAA GAC GGG TGT TCA CTC CGA CTG CAA CAG 1689
      E   R   F   L   Q   G   V   F   Q   E   D   P   E   W   R   A   L   Q   E   R    583
     GAG CGC TTC CTC CAG GGG GTT TTC CAG GAA GAC CCT GAA TGG AGG GCC CTG CAG GAG AGG 1749
      Y   L   W   H   I   P   L   T   Y   S   T   S   S   N   V   I   H   R   H    603
     TAC CTG TGG CAT ATC CCA TTG ACC TAC TCC ACG AGT TCT TCT AAT GTG ATC CAC AGA CAC 1809
      I   L   K   S   K   T   D   T   L   D   L   P   E   K   T   S   W   V   K   F    623
     ATT CTA AAA TCA AAG ACA GAT ACT CTG GAT CTA CCT GAA AAG ACC AGT TGG GTG AAA TTT 1869
      N   V   D   S   N   G   Y   Y   I   V   H   Y   E   G   H   G   W   D   Q   L    643
     AAT GTG GAC TCA AAT GGT TAC TAC ATC GTT CAC TAT GAG GGT CAT GGA TGG GAC CAA CTC 1929
      I   T   Q   L   N   Q   N   H   T   L   L   R   P   K   D   R   V   G   L   I    663
     ATT ACA CAG CTG AAT CAG AAC CAC ACA CTT CTC AGA CCT AAG GAC AGA GTA GGT CTG ATT 1989
      H   D   V   F   Q   L   V   G   A   G   R   L   T   L   D   K   A   L   D   M    683
     CAT GAT GTG TTT CAG CTA GTT GGT GCA GGG AGA CTG ACC CTA GAC AAA GCT CTT GAC ATG 2049
      T   Y   Y   L   Q   H   E   T   S   S   P   A   L   L   E   G   L   S   Y   L    703
     ACT TAC TAC CTC CAA CAT GAA ACA AGC AGC CCC GCA CTT CTC GAA GGT CTG AGT TAC TTG 2109
      E   S   F   Y   H   M   M   D   R   R   N   I   S   D   I   S   E   N   L   K    723
     GAA TCG TTT TAC CAC ATG ATG GAC AGA AGG AAT ATT TCA GAT ATC TCT GAA AAC CTC AAG 2169
      R   Y   L   L   Q   Y   F   K   P   V   I   D   R   Q   S   W   S   D   K   G    743
     CGT TAC CTT CTT CAG TAT TTT AAG CCA GTG ATT GAC AGG CAA AGC TGG AGT GAC AAG GGC 2229
      S   V   W   D   R   M   L   R   S   A   L   L   K   L   A   C   D   L   N   H    763
     TCA GTC TGG GAC AGG ATG CTC CGC TCG GCT CTC TTG AAG CTG GCC TGT GAC CTG AAC CAT 2289
      A   P   C   I   Q   K   A   A   E   L   F   S   Q   W   M   E   S   S   G   K    783
     GCT CCT TGC ATC CAG AAA GCT GCT GAA CTC TTC TCC CAG TGG ATG GAA TCC AGT GGA AAA 2349
      L   N   I   P   T   D   V   L   K   I   V   Y   S   V   G   A   Q   T   L   A    803
     TTA AAT ATA CCA ACA GAT GTT TTA AAG ATT GTG TAT TCT GTG GCT CAG ACA ACA GCA 2409
      G   W   N   Y   L   L   E   Q   Y   E   L   S   M   S   S   A   E   Q   N   K    823
     GGA TGG AAT TAC CTT TTA GAG CAA TAT GAA CTG TCA ATG TCA AGT GCT GAA CAA AAC AAA 2469
```

FIG. 1B.

```
     I   L   Y   A   L   S   T   S   K   H   Q   E   K   L   L   K   L   I   E   L    843
    ATT CTG TAT GCT TTG TCA ACG AGC AAG CAT CAG GAA AAG TTA CTG AAG TTA ATT GAA CTA   2529
     G   M   E   G   K   V   I   K   T   Q   N   L   A   A   L   L   H   A   I   A    863
    GGA ATG GAA GGA AAG GTT ATC AAG ACA CAG AAC TTG GCA GCT CTC CTT CAT GCG ATT GCC   2589
     R   R   P   K   G   Q   Q   L   A   W   D   F   V   R   E   N   W   T   H   L    883
    AGA CGT CCA AAG GGG CAG CAA CTA GCA TGG GAT TTT GTA AGA GAA AAT TGG ACC CAT CTT   2649
     L   K   K   F   D   L   G   S   Y   D   I   R   M   I   I   S   G   T   T   A    903
    CTG AAA AAA TTT GAC TTG GGC TCA TAT GAC ATA AGG ATG ATC ATC TCT GGC ACA ACA GCT   2709
     H   F   S   S   K   D   K   L   Q   E   V   K   L   F   F   E   S   L   E   A    923
    CAC TTT TCT TCC AAG GAT AAG TTG CAA GAG GTG AAA CTA TTT TTT GAA TCT CTT GAG GCT   2769
     Q   G   S   H   L   D   I   F   Q   T   V   L   E   T   I   T   K   N   I   K    943
    CAA GGA TCA CAT CTG GAT ATT TTT CAA ACT GTT CTG GAA ACG ATA ACC AAA AAT ATA AAA   2829
     W   L   E   K   N   L   P   T   L   R   T   W   L   M   V   N   T   *            961
    TGG CTG GAG AAG AAT CTT CCG ACT CTG AGG ACT TGG CTA ATG GTT AAT ACT TAA            2883
    ATGGTCAATAGAAAAAGTAGGCTGGGCGCGGTGGCTCACGCCTGTAATCCCAGCACTTTGGGAGGCTGAGAAGGGCGGA
    TCACGAGGTCAGGAGATGGAGACCATCCTGGCTAACACGGTGAGACCCCGTCTCCGCTAAAAATACAAAAAATTAGCCG
    GGCATGGTGGCAGGTGCCTGTAGTCCCAGCTACTCGGCAGGCTGCAGCAGGAAAATGGCATAAACCCGGGAGGTGGAGC
    TTGCAGTGAGCCGAGATTGCACCACTGCATTCCAGCCTGGGTGACTGAGCGAGACTCTGTCTCAAAAAAAAAAAAAAAA
    AAAAAAAAAAAAAAAAAAAAAAA
```

FIG. 1C.

Prosite Pattern Matches for sequence7420

>PS00001/PDOC00001/ASN_GLYCOSYLATION N-glycosylation site.

Query: 85  NLTS  88
Query: 103  NATQ  106
Query: 119  NATL  122
Query: 219  NFSI  222
Query: 294  NQTH  297

FIG. 4A.

Query: 405    NATY    408
Query: 431    NSSR    434
Query: 650    NHTL    653
Query: 714    NISD    717
Query: 879    NWTH    882

>PS00004/PDOC00004/CAMP_PHOSPHO_SITE cAMP - and cGMP-dependent protein kinase phosphorylation site.

Query: 225    RRES    228
Query: 483    KKFS    486

>PS00005/PDOC00005/PKC_PHOSPHO_SITE Protein kinase C phosphorylation site.

Query: 10     SHR     12
Query: 94     SEK     96
Query: 183    TYR     185
Query: 221    SIK     223
Query: 256    TVK     258
Query: 303    SLK     305
Query: 343    TYR     345
Query: 359    SDK     361
Query: 432    SSR     434
Query: 486    SYR     488
Query: 558    SLR     560
Query: 740    SDK     742
Query: 781    SGK     783
Query: 830    TSK     832
Query: 906    SSK     908
Query: 951    TLR     853

>PS0006/PDOC0006/CK2_PHOSPHO_SITE Casein kinase II phosphorylation site.

Query: 57     TNGE    60
Query: 87     TSLD    90
Query: 124    SEED    127
Query: 197    TDFE    200
Query: 321    SKLD    324
Query: 343    TYRE    346
Query: 357    SASD    360
Query: 407    TYPE    410
Query: 502    SCLE    505
Query: 607    SKTD    610
Query: 701    SYLE    704
Query: 738    SWSD    741
Query: 744    SVVD    747
Query: 817    SSAE    820

FIG. 4B.

Query: 906  SSKD  909
Query: 926  SHLD  929
Query: 933  TVLE  936

>PS00007/PDOC00007/TYR_PHOSPHO_SITE Tyrosine kinase phosphorylation site.

Query: 312  KYFDIYY   318
Query: 622  KFNVDSNGY 630
Query: 679  KALDMTYY  686
Query: 885  KKFDLGSY  892

>PS0008/PDOC0008/MYRISTYL N-myristoylation site.

Query: 281  GVKVSI  286
Query: 334  GAMENV  339
Query: 378  GNLVTM  383
Query: 512  GVCHSD  517
Query: 798  GAQTTA  803
Query: 868  GQQLAW  873

>PS00142/PDOC00129/ZINC_PROTEASE Neutral zinc metallopeptidases, zinc-binding region signature.

Query: 367  VIAHELAHQV  376

FIG. 4C.

```
                        SEQUENCE LISTING

<160> NUMBER OF SEQ ID NOS: 3

<210> SEQ ID NO 1
<211> LENGTH: 960
<212> TYPE: PRT
<213> ORGANISM: Homo sapiens

<400> SEQUENCE: 1

Met Phe His Ser Ser Ala Met Val Asn Ser His Arg Lys Pro Met Phe
1               5                   10                  15

Asn Ile His Arg Gly Phe Tyr Cys Leu Thr Ala Ile Leu Pro Gln Ile
            20                  25                  30

Cys Ile Cys Ser Gln Phe Ser Val Pro Ser Ser Tyr His Phe Thr Glu
        35                  40                  45

Asp Pro Gly Ala Phe Pro Val Ala Thr Asn Gly Glu Arg Phe Pro Trp
    50                  55                  60

Gln Glu Leu Arg Leu Pro Ser Val Val Ile Pro Leu His Tyr Asp Leu
65                  70                  75                  80

Phe Val His Pro Asn Leu Thr Ser Leu Asp Phe Val Ala Ser Glu Lys
                85                  90                  95

Ile Glu Val Leu Val Ser Asn Ala Thr Gln Phe Ile Ile Leu His Ser
            100                 105                 110

Lys Asp Leu Glu Ile Thr Asn Ala Thr Leu Gln Ser Glu Glu Asp Ser
        115                 120                 125

Arg Tyr Met Lys Pro Gly Lys Glu Leu Lys Val Leu Ser Tyr Pro Ala
```

-continued

```
            130                 135                 140
His Glu Gln Ile Ala Leu Leu Val Pro Glu Lys Leu Thr Pro His Leu
145                 150                 155                 160

Lys Tyr Tyr Val Ala Met Asp Phe Gln Ala Lys Leu Gly Asp Gly Phe
                165                 170                 175

Glu Gly Phe Tyr Lys Ser Thr Tyr Arg Thr Leu Gly Gly Glu Thr Arg
                180                 185                 190

Ile Leu Ala Val Thr Asp Phe Glu Pro Thr Gln Ala Arg Met Ala Phe
                195                 200                 205

Pro Cys Phe Asp Glu Pro Leu Phe Lys Ala Asn Phe Ser Ile Lys Ile
210                 215                 220

Arg Arg Glu Ser Arg His Ile Ala Leu Ser Asn Met Pro Lys Val Lys
225                 230                 235                 240

Thr Ile Glu Leu Glu Gly Gly Leu Leu Glu Asp His Phe Glu Thr Thr
                245                 250                 255

Val Lys Met Ser Thr Tyr Leu Val Ala Tyr Ile Val Cys Asp Phe His
                260                 265                 270

Ser Leu Ser Gly Phe Thr Ser Ser Gly Val Lys Val Ser Ile Tyr Ala
                275                 280                 285

Ser Pro Asp Lys Arg Asn Gln Thr His Tyr Ala Leu Gln Ala Ser Leu
290                 295                 300

Lys Leu Leu Asp Phe Tyr Glu Lys Tyr Phe Asp Ile Tyr Tyr Pro Leu
305                 310                 315                 320

Ser Lys Leu Asp Leu Ile Ala Ile Pro Asp Phe Ala Pro Gly Ala Met
                325                 330                 335

Glu Asn Trp Gly Leu Ile Thr Tyr Arg Glu Thr Ser Leu Leu Phe Asp
                340                 345                 350

Pro Lys Thr Ser Ser Ala Ser Asp Lys Leu Trp Val Thr Arg Val Ile
                355                 360                 365

Ala His Glu Leu Ala His Gln Trp Phe Gly Asn Leu Val Thr Met Glu
                370                 375                 380

Trp Trp Asn Asp Ile Trp Leu Lys Glu Gly Phe Ala Lys Tyr Met Glu
385                 390                 395                 400

Leu Ile Ala Val Asn Ala Thr Tyr Pro Glu Leu Gln Phe Asp Asp Tyr
                405                 410                 415

Phe Leu Asn Val Cys Phe Glu Val Ile Thr Lys Asp Ser Leu Asn Ser
                420                 425                 430

Ser Arg Pro Ile Ser Lys Pro Ala Glu Thr Pro Thr Gln Ile Gln Glu
                435                 440                 445

Met Phe Asp Glu Val Ser Tyr Asn Lys Gly Ala Cys Ile Leu Asn Met
450                 455                 460

Leu Lys Asp Phe Leu Gly Glu Glu Lys Phe Gln Lys Gly Ile Ile Gln
465                 470                 475                 480

Tyr Leu Lys Lys Phe Ser Tyr Arg Asn Ala Lys Asn Asp Asp Leu Trp
                485                 490                 495

Ser Ser Leu Ser Asn Ser Cys Leu Glu Ser Asp Phe Thr Ser Gly Gly
                500                 505                 510

Val Cys His Ser Asp Pro Lys Met Thr Ser Asn Met Leu Ala Phe Leu
                515                 520                 525

Gly Glu Asn Ala Glu Val Lys Glu Met Met Thr Thr Trp Thr Leu Gln
530                 535                 540

Lys Gly Ile Pro Leu Leu Val Val Lys Gln Asp Gly Cys Ser Leu Arg
545                 550                 555                 560
```

```
Leu Gln Gln Glu Arg Phe Leu Gly Val Phe Gln Asp Pro Glu
            565                 570                 575

Trp Arg Ala Leu Gln Glu Arg Tyr Leu Trp His Ile Pro Leu Thr Tyr
            580                 585                 590

Ser Thr Ser Ser Ser Asn Val Ile His Arg His Ile Leu Lys Ser Lys
            595                 600                 605

Thr Asp Thr Leu Asp Leu Pro Glu Lys Thr Ser Trp Val Lys Phe Asn
            610                 615                 620

Val Asp Ser Asn Gly Tyr Tyr Ile Val His Tyr Glu Gly His Gly Trp
625                 630                 635                 640

Asp Gln Leu Ile Thr Gln Leu Asn Gln Asn His Thr Leu Leu Arg Pro
            645                 650                 655

Lys Asp Arg Val Gly Leu Ile His Asp Val Phe Gln Leu Val Gly Ala
            660                 665                 670

Gly Arg Leu Thr Leu Asp Lys Ala Leu Asp Met Thr Tyr Tyr Leu Gln
            675                 680                 685

His Glu Thr Ser Ser Pro Ala Leu Leu Glu Gly Leu Ser Tyr Leu Glu
            690                 695                 700

Ser Phe Tyr His Met Met Asp Arg Arg Asn Ile Ser Asp Ile Ser Glu
705                 710                 715                 720

Asn Leu Lys Arg Tyr Leu Leu Gln Tyr Phe Lys Pro Val Ile Asp Arg
            725                 730                 735

Gln Ser Trp Ser Asp Lys Gly Ser Val Trp Asp Arg Met Leu Arg Ser
            740                 745                 750

Ala Leu Leu Lys Leu Ala Cys Asp Leu Asn His Ala Pro Cys Ile Gln
            755                 760                 765

Lys Ala Ala Glu Leu Phe Ser Gln Trp Met Glu Ser Ser Gly Lys Leu
            770                 775                 780

Asn Ile Pro Thr Asp Val Leu Lys Ile Val Tyr Ser Val Gly Ala Gln
785                 790                 795                 800

Thr Thr Ala Gly Trp Asn Tyr Leu Leu Glu Gln Tyr Glu Leu Ser Met
            805                 810                 815

Ser Ser Ala Glu Gln Asn Lys Ile Leu Tyr Ala Leu Ser Thr Ser Lys
            820                 825                 830

His Gln Glu Lys Leu Leu Lys Leu Ile Glu Leu Gly Met Glu Gly Lys
            835                 840                 845

Val Ile Lys Thr Gln Asn Leu Ala Ala Leu Leu His Ala Ile Ala Arg
850                 855                 860

Arg Pro Lys Gly Gln Gln Leu Ala Trp Asp Phe Val Arg Glu Asn Trp
865                 870                 875                 880

Thr His Leu Leu Lys Lys Phe Asp Leu Gly Ser Tyr Asp Ile Arg Met
            885                 890                 895

Ile Ile Ser Gly Thr Thr Ala His Phe Ser Ser Lys Asp Lys Leu Gln
            900                 905                 910

Glu Val Lys Leu Phe Phe Glu Ser Leu Glu Ala Gln Gly Ser His Leu
            915                 920                 925

Asp Ile Phe Gln Thr Val Leu Glu Thr Ile Thr Lys Asn Ile Lys Trp
            930                 935                 940

Leu Glu Lys Asn Leu Pro Thr Leu Arg Thr Trp Leu Met Val Asn Thr
945                 950                 955                 960

<210> SEQ ID NO 2
<211> LENGTH: 3366
<212> TYPE: DNA
<213> ORGANISM: Homo sapiens
```

-continued

```
<220> FEATURE:
<221> NAME/KEY: CDS
<222> LOCATION: (146)...(3028)

<400> SEQUENCE: 2
ccccgcgtcc ggcatgattt aagattaaat tcatgtattg aaaatattgt tcagacccca      60
tgtgacataa ctggagccag tgcagtgcca tgaagaacta cgagattagc ctggatatta    120
acttgtcttc tagagaatag atttc atg ttc cat tct tct gca atg gtt aat      172
                            Met Phe His Ser Ser Ala Met Val Asn
                             1               5 tca cac aga aaa cca atg ttt aac att cac aga gga ttt tac tgc tta      220
Ser His Arg Lys Pro Met Phe Asn Ile His Arg Gly Phe Tyr Cys Leu
 10              15                  20                  25 aca gcc atc ttg ccc caa ata tgc att tgt tct cag ttc tca gtg cca      268
Thr Ala Ile Leu Pro Gln Ile Cys Ile Cys Ser Gln Phe Ser Val Pro
                 30                  35                  40 tct agt tat cac ttc act gag gat cct ggg gct ttc cca gta gcc act      316
Ser Ser Tyr His Phe Thr Glu Asp Pro Gly Ala Phe Pro Val Ala Thr
             45                  50                  55 aat ggg gaa cga ttt cct tgg cag gag cta agg ctc ccc agt gtg gtc      364
Asn Gly Glu Arg Phe Pro Trp Gln Glu Leu Arg Leu Pro Ser Val Val
         60                  65                  70 att cct ctc cat tat gac ctc ttt gtc cac ccc aat ctc acc tct ctg      412
Ile Pro Leu His Tyr Asp Leu Phe Val His Pro Asn Leu Thr Ser Leu
     75                  80                  85 gac ttt gtt gca tct gag aag atc gaa gtc ttg gtc agc aat gct acc      460
Asp Phe Val Ala Ser Glu Lys Ile Glu Val Leu Val Ser Asn Ala Thr
 90                  95                 100                 105 cag ttt atc atc ttg cac agc aaa gat ctt gaa atc acg aat gcc acc      508
Gln Phe Ile Ile Leu His Ser Lys Asp Leu Glu Ile Thr Asn Ala Thr
                110                 115                 120 ctt cag tca gag gaa gat tca aga tac atg aaa cca gga aaa gaa ctg      556
Leu Gln Ser Glu Glu Asp Ser Arg Tyr Met Lys Pro Gly Lys Glu Leu
            125                 130                 135 aaa gtt ttg agt tac cct gct cat gaa caa att gca ctg ctg gtt cca      604
Lys Val Leu Ser Tyr Pro Ala His Glu Gln Ile Ala Leu Leu Val Pro
        140                 145                 150 gag aaa ctt acg cct cac ctg aaa tac tat gtg gct atg gac ttc caa      652
Glu Lys Leu Thr Pro His Leu Lys Tyr Tyr Val Ala Met Asp Phe Gln
    155                 160                 165 gcc aag tta ggt gat ggc ttt gaa ggg ttt tat aaa agc aca tac aga      700
Ala Lys Leu Gly Asp Gly Phe Glu Gly Phe Tyr Lys Ser Thr Tyr Arg
170                 175                 180                 185 act ctt ggt ggt gaa aca aga att ctt gca gta aca gat ttt gag cca      748
Thr Leu Gly Gly Glu Thr Arg Ile Leu Ala Val Thr Asp Phe Glu Pro
                190                 195                 200 acc cag gca cgc atg gct ttc cct tgc ttt gat gaa ccg ttg ttc aaa      796
Thr Gln Ala Arg Met Ala Phe Pro Cys Phe Asp Glu Pro Leu Phe Lys
            205                 210                 215 gcc aac ttt tca atc aag ata cga aga gag agc agg cat att gca cta      844
Ala Asn Phe Ser Ile Lys Ile Arg Arg Glu Ser Arg His Ile Ala Leu
        220                 225                 230 tcc aac atg cca aag gtt aag aca att gaa ctt gaa gga ggt ctt ttg      892
Ser Asn Met Pro Lys Val Lys Thr Ile Glu Leu Glu Gly Gly Leu Leu
    235                 240                 245 gaa gat cac ttt gaa act act gta aaa atg agt aca tac ctt gta gcc      940
Glu Asp His Phe Glu Thr Thr Val Lys Met Ser Thr Tyr Leu Val Ala
250                 255                 260                 265 tac ata gtt tgt gat ttc cac tct ctg agt ggc ttc act tca tca ggg      988
Tyr Ile Val Cys Asp Phe His Ser Leu Ser Gly Phe Thr Ser Ser Gly
```

```
                              270                 275                 280
gtc aag gtg tcc atc tat gca tcc cca gac aaa cgg aat caa aca cat         1036
Val Lys Val Ser Ile Tyr Ala Ser Pro Asp Lys Arg Asn Gln Thr His
            285                 290                 295 tat gct ttg cag gca tca ctg aag cta ctt gat ttt tat gaa aag tac         1084
Tyr Ala Leu Gln Ala Ser Leu Lys Leu Leu Asp Phe Tyr Glu Lys Tyr
        300                 305                 310 ttt gat atc tac tat cca ctc tcc aaa ctg gat tta att gct att cct         1132
Phe Asp Ile Tyr Tyr Pro Leu Ser Lys Leu Asp Leu Ile Ala Ile Pro
    315                 320                 325 gac ttt gca cct gga gcc atg gaa aat tgg ggc ctc att aca tat agg         1180
Asp Phe Ala Pro Gly Ala Met Glu Asn Trp Gly Leu Ile Thr Tyr Arg
330                 335                 340                 345 gag acg tca ctg ctt ttt gac ccc aag acc tct tct gct tcc gat aaa         1228
Glu Thr Ser Leu Leu Phe Asp Pro Lys Thr Ser Ser Ala Ser Asp Lys
                350                 355                 360 ctg tgg gtc acc aga gtc ata gcc cat gaa ctg gcg cac cag tgg ttt         1276
Leu Trp Val Thr Arg Val Ile Ala His Glu Leu Ala His Gln Trp Phe
            365                 370                 375 ggc aac ctg gtc aca atg gaa tgg tgg aat gat att tgg ctt aag gag         1324
Gly Asn Leu Val Thr Met Glu Trp Trp Asn Asp Ile Trp Leu Lys Glu
        380                 385                 390 ggt ttt gca aaa tac atg gaa ctt atc gct gtt aat gct aca tat cca         1372
Gly Phe Ala Lys Tyr Met Glu Leu Ile Ala Val Asn Ala Thr Tyr Pro
    395                 400                 405 gag ctg caa ttt gat gac tat ttt ttg aat gtg tgt ttt gaa gta att         1420
Glu Leu Gln Phe Asp Asp Tyr Phe Leu Asn Val Cys Phe Glu Val Ile
410                 415                 420                 425 aca aaa gat tca ttg aat tca tcc cgc cct atc tcc aaa cca gcg gaa         1468
Thr Lys Asp Ser Leu Asn Ser Ser Arg Pro Ile Ser Lys Pro Ala Glu
                430                 435                 440 acc ccg act caa ata cag gaa atg ttt gat gaa gtt tcc tat aac aag         1516
Thr Pro Thr Gln Ile Gln Glu Met Phe Asp Glu Val Ser Tyr Asn Lys
            445                 450                 455 gga gct tgt att ttg aat atg ctc aag gat ttt ctg ggt gag gag aaa         1564
Gly Ala Cys Ile Leu Asn Met Leu Lys Asp Phe Leu Gly Glu Glu Lys
        460                 465                 470 ttc cag aaa gga ata att cag tac tta aag aag ttc agc tat aga aat         1612
Phe Gln Lys Gly Ile Ile Gln Tyr Leu Lys Lys Phe Ser Tyr Arg Asn
    475                 480                 485 gct aag aat gat gac ttg tgg agc agt ctg tca aat agt tgt tta gaa         1660
Ala Lys Asn Asp Asp Leu Trp Ser Ser Leu Ser Asn Ser Cys Leu Glu
490                 495                 500                 505 agt gat ttt aca tct ggt gga gtt tgt cat tcg gat ccc aag atg aca         1708
Ser Asp Phe Thr Ser Gly Gly Val Cys His Ser Asp Pro Lys Met Thr
                510                 515                 520 agt aac atg ctc gcc ttt ctg ggg gaa aat gca gag gtc aaa gag atg         1756
Ser Asn Met Leu Ala Phe Leu Gly Glu Asn Ala Glu Val Lys Glu Met
            525                 530                 535 atg act aca tgg act ctc cag aaa gga atc ccc ctg ctg gtg gtt aaa         1804
Met Thr Thr Trp Thr Leu Gln Lys Gly Ile Pro Leu Leu Val Val Lys
        540                 545                 550 caa gac ggg tgt tca ctc cga ctg caa cag gag cgc ttc ctc cag ggg         1852
Gln Asp Gly Cys Ser Leu Arg Leu Gln Gln Glu Arg Phe Leu Gln Gly
    555                 560                 565 gtt ttc cag gaa gac cct gaa tgg agg gcc ctg cag gag agg tac ctg         1900
Val Phe Gln Glu Asp Pro Glu Trp Arg Ala Leu Gln Glu Arg Tyr Leu
570                 575                 580                 585 tgg cat atc cca ttg acc tac tcc acg agt tct tct aat gtg atc cac         1948
Trp His Ile Pro Leu Thr Tyr Ser Thr Ser Ser Ser Asn Val Ile His
```

```
                    590                 595                 600
aga cac att cta aaa tca aag aca gat act ctg gat cta cct gaa aag     1996
Arg His Ile Leu Lys Ser Lys Thr Asp Thr Leu Asp Leu Pro Glu Lys
            605                 610                 615 acc agt tgg gtg aaa ttt aat gtg gac tca aat ggt tac tac atc gtt     2044
Thr Ser Trp Val Lys Phe Asn Val Asp Ser Asn Gly Tyr Tyr Ile Val
        620                 625                 630 cac tat gag ggt cat gga tgg gac caa ctc att aca cag ctg aat cag     2092
His Tyr Glu Gly His Gly Trp Asp Gln Leu Ile Thr Gln Leu Asn Gln
    635                 640                 645 aac cac aca ctt ctc aga cct aag gac aga gta ggt ctg att cat gat     2140
Asn His Thr Leu Leu Arg Pro Lys Asp Arg Val Gly Leu Ile His Asp
650                 655                 660                 665 gtg ttt cag cta gtt ggt gca ggg aga ctg acc cta gac aaa gct ctt     2188
Val Phe Gln Leu Val Gly Ala Gly Arg Leu Thr Leu Asp Lys Ala Leu
                670                 675                 680 gac atg act tac tac ctc caa cat gaa aca agc agc ccc gca ctt ctc     2236
Asp Met Thr Tyr Tyr Leu Gln His Glu Thr Ser Ser Pro Ala Leu Leu
            685                 690                 695 gaa ggt ctg agt tac ttg gaa tcg ttt tac cac atg atg gac aga agg     2284
Glu Gly Leu Ser Tyr Leu Glu Ser Phe Tyr His Met Met Asp Arg Arg
        700                 705                 710 aat att tca gat atc tct gaa aac ctc aag cgt tac ctt ctt cag tat     2332
Asn Ile Ser Asp Ile Ser Glu Asn Leu Lys Arg Tyr Leu Leu Gln Tyr
    715                 720                 725 ttt aag cca gtg att gac agg caa agc tgg agt gac aag ggc tca gtc     2380
Phe Lys Pro Val Ile Asp Arg Gln Ser Trp Ser Asp Lys Gly Ser Val
730                 735                 740                 745 tgg gac agg atg ctc cgc tcg gct ctc ttg aag ctg gcc tgt gac ctg     2428
Trp Asp Arg Met Leu Arg Ser Ala Leu Leu Lys Leu Ala Cys Asp Leu
                750                 755                 760 aac cat gct cct tgc atc cag aaa gct gct gaa ctc ttc tcc cag tgg     2476
Asn His Ala Pro Cys Ile Gln Lys Ala Ala Glu Leu Phe Ser Gln Trp
            765                 770                 775 atg gaa tcc agt gga aaa tta aat ata cca aca gat gtt tta aag att     2524
Met Glu Ser Ser Gly Lys Leu Asn Ile Pro Thr Asp Val Leu Lys Ile
        780                 785                 790 gtg tat tct gtg ggt gct cag aca aca gca gga tgg aat tac ctt tta     2572
Val Tyr Ser Val Gly Ala Gln Thr Thr Ala Gly Trp Asn Tyr Leu Leu
    795                 800                 805 gag caa tat gaa ctg tca atg tca agt gct gaa caa aac aaa att ctg     2620
Glu Gln Tyr Glu Leu Ser Met Ser Ser Ala Glu Gln Asn Lys Ile Leu
810                 815                 820                 825 tat gct ttg tca acg agc aag cat cag gaa aag tta ctg aag tta att     2668
Tyr Ala Leu Ser Thr Ser Lys His Gln Glu Lys Leu Leu Lys Leu Ile
                830                 835                 840 gaa cta gga atg gaa gga aag gtt atc aag aca cag aac ttg gca gct     2716
Glu Leu Gly Met Glu Gly Lys Val Ile Lys Thr Gln Asn Leu Ala Ala
            845                 850                 855 ctc ctt cat gcg att gcc aga cgt cca aag ggg cag caa cta gca tgg     2764
Leu Leu His Ala Ile Ala Arg Arg Pro Lys Gly Gln Gln Leu Ala Trp
        860                 865                 870 gat ttt gta aga gaa aat tgg acc cat ctt ctg aaa aaa ttt gac ttg     2812
Asp Phe Val Arg Glu Asn Trp Thr His Leu Leu Lys Lys Phe Asp Leu
    875                 880                 885 ggc tca tat gac ata agg atg atc atc tct ggc aca aca gct cac ttt     2860
Gly Ser Tyr Asp Ile Arg Met Ile Ile Ser Gly Thr Thr Ala His Phe
890                 895                 900                 905 tct tcc aag gat aag ttg caa gag gtg aaa cta ttt ttt gaa tct ctt     2908
Ser Ser Lys Asp Lys Leu Gln Glu Val Lys Leu Phe Phe Glu Ser Leu
```

-continued

|  | 910 |  |  |  | 915 |  |  |  | 920 |  |  |  |  |
|---|---|---|---|---|---|---|---|---|---|---|---|---|---|
| gag | gct | caa | gga | tca | cat | ctg | gat | att | ttt | caa | act | gtt | ctg gaa acg | 2956 |
| Glu | Ala | Gln | Gly | Ser | His | Leu | Asp | Ile | Phe | Gln | Thr | Val | Leu Glu Thr |
|  |  |  |  | 925 |  |  |  | 930 |  |  |  | 935 |  |
| ata | acc | aaa | aat | ata | aaa | tgg | ctg | gag | aag | aat | ctt | ccg | act ctg agg | 3004 |
| Ile | Thr | Lys | Asn | Ile | Lys | Trp | Leu | Glu | Lys | Asn | Leu | Pro | Thr Leu Arg |
|  |  |  | 940 |  |  |  |  | 945 |  |  |  | 950 |  |
| act | tgg | cta | atg | gtt | aat | act | taa | atggtcaata gaaaaagtag gctgggcgcg | 3058 |
| Thr | Trp | Leu | Met | Val | Asn | Thr | * |  |
|  | 955 |  |  |  | 960 |  |  |  | gtggctcacg cctgtaatcc cagcactttg ggaggctgag aagggcggat cacgaggtca    3118
ggagatggag accatcctgg ctaacacggt gagaccccgt ctccgctaaa atacaaaaaa    3178
attagccggg catggtggca ggtgcctgta gtcccagcta ctcggcaggc tgcagcagga    3238
aaatggcata acccgggag gtggagcttg cagtgagccg agattgcacc actgcattcc    3298
agcctgggtg actgagcgag actctgtctc aaaaaaaaaa aaaaaaaaaa aaaaaaaaaa    3358
aaaaaaaa                                                             3366

<210> SEQ ID NO 3
<211> LENGTH: 2883
<212> TYPE: DNA
<213> ORGANISM: homo sapiens

<400> SEQUENCE: 3
atgttccatt cttctgcaat ggttaattca cacagaaaac caatgtttaa cattcacaga      60
ggattttact gcttaacagc catcttgccc caaatatgca tttgttctca gttctcagtg     120
ccatctagtt atcacttcac tgaggatcct ggggctttcc cagtagccac taatggggaa     180
cgatttcctt ggcaggagct aaggctcccc agtgtggtca ttcctctcca ttatgacctc     240
tttgtccacc ccaatctcac ctctctggac tttgttgcat ctgagaagat cgaagtcttg     300
gtcagcaatg ctacccagtt tatcatcttg cacagcaaag atcttgaaat cacgaatgcc     360
acccttcagt cagaggaaga ttcaagatac atgaaaccag aaaagaact gaaagttttg     420
agttaccctg ctcatgaaca aattgcactg ctggttccag agaaacttac gcctcacctg     480
aaatactatg tggctatgga cttccaagcc aagttaggtg atggctttga agggttttat     540
aaaagcacat acagaactct tggtggtgaa acaagaattc ttgcagtaac agattttgag     600
ccaacccagg cacgcatggc tttcccttgc tttgatgaac cgttgttcaa agccaacttt     660
tcaatcaaga tacgaagaga gagcaggcat attgcactat ccaacatgcc aaaggttaag     720
acaattgaac ttgaaggagg tcttttggaa gatcactttg aaactactgt aaaaatgagt     780
acatacctg tagcctacat agtttgtgat ttccactctc tgagtggctt cacttcatca     840
ggggtcaagg tgtccatcta tgcatcccca gacaaacgga atcaaacaca ttatgctttg     900
caggcatcac tgaagctact tgatttttat gaaaagtact tgatatcta ctatccactc     960
tccaaactgg atttaattgc tattcctgac tttgcacctg gagccatgga aaattggggc    1020
ctcattacat ataggagac gtcactgctt tttgaccca gacctcttc tgcttccgat    1080
aaactgtggg tcaccagagt catagcccat gaactggcgc accagtggtt tggcaacctg    1140
gtcacaatgg aatggtggaa tgatatttgg cttaaggagg ttttgcaaaa tacatggaa    1200
cttatcgctg ttaatgctac atatccagag ctgcaatttg atgactattt tttgaatgtg    1260
tgttttgaag taattacaaa agattcattg aattcatccc gccctatctc caaaccagcg    1320
gaaaccccga ctcaaatacaa ggaaatgttt gatgaagttt cctataacaa gggagcttgt    1380

-continued

```
attttgaata tgctcaagga ttttctgggt gaggagaaat tccagaaagg aataattcag    1440
tacttaaaga agttcagcta tagaaatgct aagaatgatg acttgtggag cagtctgtca    1500
aatagttgtt tagaaagtga ttttacatct ggtggagttt gtcattcgga tcccaagatg    1560
acaagtaaca tgctcgcctt tctggggaa aatgcagagg tcaaagagat gatgactaca    1620
tggactctcc agaaaggaat cccctgctg gtggttaaac aagacgggtg ttcactccga    1680
ctgcaacagg agcgcttcct ccaggggt ttccaggaag accctgaatg gagggccctg    1740
caggagaggt acctgtggca tatcccattg acctactcca cgagttcttc taatgtgatc    1800
cacagacaca ttctaaaatc aaagacagat actctggatc tacctgaaaa gaccagttgg    1860
gtgaaattta atgtggactc aaatggttac tacatcgttc actatgaggg tcatggatgg    1920
gaccaactca ttacacagct gaatcagaac cacacacttc tcagacctaa ggacagagta    1980
ggtctgattc atgatgtgtt tcagctagtt ggtgcaggga gactgaccct agacaaagct    2040
cttgacatga cttactacct ccaacatgaa acaagcagcc ccgcacttct cgaaggtctg    2100
agttacttgg aatcgtttta ccacatgatg gacagaagga atatttcaga tatctctgaa    2160
aacctcaagc gttaccttct tcagtatttt aagccagtga ttgacaggca aagctggagt    2220
gacaagggct cagtctggga caggatgctc cgctcggctc tcttgaagct ggcctgtgac    2280
ctgaaccatg ctccttgcat ccagaaagct gctgaactct tctcccagtg gatggaatcc    2340
agtggaaaat taaatatacc aacagatgtt ttaaagattg tgtattctgt gggtgctcag    2400
acaacagcag gatggaatta ccttttagag caatatgaac tgtcaatgtc aagtgctgaa    2460
caaaacaaaa ttctgtatgc tttgtcaacg agcaagcatc aggaaaagtt actgaagtta    2520
attgaactag gaatggaagg aaaggttatc aagacacaga acttggcagc tctccttcat    2580
gcgattgcca gacgtccaaa ggggcagcaa ctagcatggg attttgtaag agaaaattgg    2640
acccatcttc tgaaaaaatt tgacttgggc tcatatgaca taaggatgat catctctggc    2700
acaacagctc acttttcttc caaggataag ttgcaagagg tgaaactatt ttttgaatct    2760
cttgaggctc aaggatcaca tctggatatt tttcaaactg ttctggaaac gataaccaaa    2820
aatataaaat ggctggagaa gaatcttccg actctgagga cttggctaat ggttaatact    2880
taa                                                                  2883
```

17867, A NOVEL HUMAN AMINOPEPTIDASE

CROSS-REFERENCE TO RELATED APPLICATIONS

This application is a division of Ser. No. 11/333,848 filed Jan. 17, 2006, which is a division of Ser. No. 10/039,073 filed Dec. 31, 2001, now issued as U.S. Pat. No. 7,034,111, which is a continuation of Ser. No. 09/345,650 filed Jun. 30, 1999, now issued as U.S. Pat. No. 6,362,324. These applications are incorporated in their entireties by reference herein.

FIELD OF THE INVENTION

The present invention relates to a newly identified human aminopeptidase. The invention also relates to polynucleotides encoding the aminopeptidase. The invention further relates to methods using the aminopeptidase polypeptides and polynucleotides as a target for diagnosis and treatment in aminopeptidase-related disorders. The invention further relates to drug-screening methods using the aminopeptidase polypeptides and polynucleotides to identify agonists and antagonists for diagnosis and treatment. The invention further encompasses agonists and antagonists based on the aminopeptidase polypeptides and polynucleotides. The invention further relates to procedures for producing the aminopeptidase polypeptides and polynucleotides.

BACKGROUND OF THE INVENTION

Proteases may function in carcinogenesis by inactivating or activating regulators of the cell cycle, differentiation, programmed cell death, or other processes affecting cancer development and/or progression. Consistent with the model involving protease activity and tumor progression, certain protease inhibitors have been shown to be effective inhibitors of carcinogenesis both in vitro and in vivo.

Aminopeptidases (APs) are a group of widely distributed exopeptidases that catalyse the hydrolysis of amino acid residues from the amino-terminus of polypeptides and proteins. The enzymes are found in plant and animal tissue, in eukaryotes and prokaryotes, and in secreted and soluble forms. Biological functions of aminopeptidases include protein maturation, terminal degradation of proteins, hormone level regulation, and cell-cycle control.

The enzymes are implicated in a host of conditions and disorders including aging, cancers, cataracts, cystic fibrosis and leukemias. In eukaryotes, APs are associated with removal of the initiator methionine. In prokaryotes the methionine is removed by methionine aminopeptidase subsequent to removal of the N-formyl group from the initiator N-formyl methionine, facilitating subsequent modifications such as N-acetylation and N-myristoylation. In *E. coli* AP-A (pepA), the xerB gene product is required for stabilization of unstable plasmid multimers.

APs are also involved in the metabolism of secreted regulatory molecules, such as hormones and neurotransmitters, and modulation of cell-cell interactions. In mammalian cells and tissues, the enzymes are apparently required for terminal stages of protein degradation, and EGF-induced cell-cycle control; and may have a role in protein turnover and selective elimination of obsolete or defective proteins. Furthermore, the enzymes are implicated in the supply of amino acids and energy during starvation and/or differentiation, and degradation of transported exogenous peptides to amino acids for nutrition. As leukotriene A4 hydrolase may be an aminopeptidase, APs may further have a role in inflammation. Industrial uses of the enzymes include modification of amino termini in recombinantly expressed proteins. See A. Taylor (1993) *TIBS* 18: 1993:167-172.

A variety of aminopeptidases have been identified from a wide variety of tissues and organisms, including zinc aminopeptidase and aminopeptidase M from rat kidney membrane; arginine aminopeptidase from liver; aminopeptidase $N^b$ from muscle; leucine aminopeptidase (LAP) from bovine and hog lens and kidney; aminopeptidase A (xerB gene product) from *E. coli*; ysc1 APE1/LAP4 and aminopeptidase A (pep4 gene product) from *S. cerevisiae*; LAP from *aeromonas*; dipeptidase from mouse ascites; methionine aminopeptidase from *salmonella, E. coli, S. cerevisiae* and hog liver; and D-amino acid aminopeptidase from *ochrobactrum anthropi* SCRC C1-38.

Of these aminopeptidases, the structure of bovine lens leucine aminopeptidase (blLAP) is well characterized and consists of a homohexamer synthesized as a large precursor, each monomer containing two thirds of the protein in a major lobe and one third in a minor lobe. The minor lobe contains the N-terminal 150 residues. All putative active site residues, presumably also the inhibitor bestatin-binding site, are found in the C-terminal lobe and include Ala-333, Asn-330, Leu360, Asp332, Asp255, Glu-334, Lys250, Asp273, Met454, Ala-451, Gly362, Thr-359, Met270, Lys262, Gly362 and Ile-421.

Many aminopeptidases are metalloenzymes, requiring divalent cations, with specificities for $Zn^{2+}$ or $Co^{2+}$; however, particular sites of certain aminopeptidases can readily utilize $Mn^{2+}$ and $Mg^{2+}$. Residues used to ligand $Zn^{2+}$ include the His His Glu and Asp Glu Lys configurations. In addition to bestatin, boronic and phosphonic acids, α-methylleucine and isoamylthioamide are identified as competitive inhibitors for most aminopeptidases. See A. Taylor (1993) *TIBS* 18: 1993: 167-172; Burley et al. (1992) *J. Mol. Biol.* 224:113-140; Taylor et al. (1993) *Biochemistry* 32:784-790.

Aminopeptidases from various organisms and various tissues within an organism have high degrees of primary sequence homology, as indicated by immunological assays. Some enzymes also exhibit very similar kinetic profiles. Direct amino acids sequence comparison of blLAP and aminopeptidase-A from *E. coli* shows 18, 44 and 35% identity for the amino- and carboxy-terminals, and the entire protein, respectively. The comparison shows 46, 66, and 60% identity for the respective regions. See Burley et al. (1992) *J. Mol. Biol.* 224:113-140.

Bovine lens leucine aminopeptidase (blLAP), bovine kidney LAP, human lens and liver LAPs, hog, lens, kidney and intestine LAPs, proline-AP, *E. coli* AP-A, AP-I and the *S. typhimurium* pepA gene product have been categorized as belonging to the family of zinc aminopeptidases which utilize the residues Asp Glu Lys for zinc binding and the active site amino acid configuration described above for bovine LAP for substrate binding. This family, possibly also including *Aeromonas* LAP, is suggested to be distinguished from zinc proteases which utilize His His Glu in zinc binding and Arg in substrate binding. The *Saccharomyces* methionine-AP is characterized to contain two zinc finger like motifs in the amino-terminus and shares little homology with blLAP. See A. Taylor (1993) *TIBS* 18: May 1993: 167-171; Watt et al. (1989) *J. Biol. Chem.* 264:5480-5487.

Leucine aminopeptidase expression is regulated at the transcriptional level, evidenced by enhancement of both activity and mRNA upon removal of serum in in vitro aged and/or transforming lens epithelial cells. Furthermore, LAP mRNA and protein is induced by interferon γ in human ACHN renal carcinoma, A549 lung carcinoma, HS153 fibroblasts and A375 melanoma. Regulation by development and growth is also implicated. The *E. coli* pepN gene is transcriptionally regulated upon anaerobiosis and phosphate starvation. Membrane bound AP-N (CD13) is expressed in a lineage-restricted manner by subsets of normal and malignant cells, apparently through regulation by physically distinct promoters. Expression of the yeast yscI product APE1 is dependent upon the levels of yscA and PEP4 gene products. Synthesis of APE1 is sensitive to media glucose levels, and the activity of yeast aminopeptidase is sensitive to substitution of ammonia rather than peptone as the source of nitrogen. See Harris et al. (1992) *J. Biol. Chem.* 267:6865-6869; Jones et al. (1982) *Genetics* 102:665-677.

Accordingly, aminopeptidases are a major target for drug action and development. Therefore, it is valuable to the field of pharmaceutical development to identify and characterize previously unknown aminopeptidases. The present invention advances the state of the art by providing a previously unidentified human aminopeptidase.

SUMMARY OF THE INVENTION

It is an object of the invention to identify novel aminopeptidases.

It is a further object of the invention to provide novel aminopeptidase polypeptides that are useful as reagents or targets in aminopeptidase assays applicable to treatment and diagnosis of aminopeptidase-related disorders.

It is a further object of the invention to provide polynucleotides corresponding to the novel aminopeptidase polypeptides that are useful as targets and reagents in aminopeptidase assays applicable to treatment and diagnosis of aminopeptidase-related disorders and useful for producing novel aminopeptidase polypeptides by recombinant methods.

A specific object of the invention is to identify compounds that act as agonists and antagonists and modulate the expression of the novel aminopeptidase.

A further specific object of the invention is to provide compounds that modulate expression of the aminopeptidase for treatment and diagnosis of aminopeptidase-related disorders.

The invention is thus based on the identification of a novel human aminopeptidase. The amino acid sequence is shown in SEQ ID NO 1. The nucleotide sequence is shown as SEQ ID NO 2.

The invention provides isolated aminopeptidase polypeptides, including a polypeptide having the amino acid sequence shown in SEQ ID NO 1 or the amino acid sequence encoded by the cDNA deposited as ATCC Patent Deposit No. PTA-1642 on Apr. 5, 2000 ("the deposited cDNA").

The invention also provides isolated aminopeptidase nucleic acid molecules having the sequence shown in SEQ ID NO 2 or in the deposited cDNA.

The invention also provides variant polypeptides having an amino acid sequence that is substantially homologous to the amino acid sequence shown in SEQ ID NO 1 or encoded by the deposited cDNA.

The invention also provides variant nucleic acid sequences that are substantially homologous to the nucleotide sequence shown in SEQ ID NO 2 or in the deposited cDNA.

The invention also provides fragments of the polypeptide shown in SEQ ID NO 1 and nucleotide sequence shown in SEQ ID NO 2, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the aminopeptidase nucleic acid molecules and polypeptides, and particularly recombinant vectors and host cells.

The invention also provides methods of making the vectors and host cells and methods for using them to produce the aminopeptidase nucleic acid molecules and polypeptides.

The invention also provides antibodies or antigen-binding fragments thereof that selectively bind the aminopeptidase polypeptides and fragments.

The invention also provides methods of screening for compounds that modulate expression or activity of the aminopeptidase polypeptides or nucleic acid (RNA or DNA).

The invention also provides a process for modulating aminopeptidase polypeptide or nucleic acid expression or activity, especially using the screened compounds. Modulation may be used to treat conditions related to aberrant activity or expression of the aminopeptidase polypeptides or nucleic acids.

The invention also provides assays for determining the activity of or the presence or absence of the aminopeptidase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1A-C shows the aminopeptidase nucleotide sequence (SEQ ID NO 2), the coding region (nucleotides 146-3028 of SEQ ID NO:2; nucleotides 1-2883 of SEQ ID NO:3) and the deduced amino acid sequence (SEQ ID NO 1).

FIG. 4A-C shows an analysis of the aminopeptidase open reading frame for amino acids corresponding to specific functional sites. The protein also contains a zinc binding region signature found in neutral zinc metallopeptidases.

DETAILED DESCRIPTION OF THE INVENTION

Polypeptides

The invention is based on the discovery of a novel human aminopeptidase. Specifically, an expressed sequence tag (EST) was selected based on homology to aminopeptidase sequences. This EST was used to design primers based on sequences that it contains and used to identify a cDNA from endothelial cell cDNA library. Positive clones were sequenced and the overlapping fragments were assembled. Analysis of the assembled sequence revealed that the cloned cDNA molecule encodes an aminopeptidase.

The invention thus relates to a novel aminopeptidase having the deduced amino acid sequence shown in FIG. 1 (SEQ ID NO 1) or having the amino acid sequence encoded by the cDNA deposited in a bacterial host with the Patent Depository of the American Type Culture Collection (ATCC), Manassas, Va., on Apr. 5, 2000 and assigned Patent Deposit No. PTA-1642.

The deposit will be maintained under the terms of the Budapest Treaty on the International Recognition of the Deposit of Microorganisms. The deposit is provided as a convenience to those of skill in the art and is not an admission that a deposit is required under 35 U.S.C. §112. The deposited sequence, as well as the polypeptides encoded by the sequence, is incorporated herein by reference and controls in the event of any conflict, such as a sequencing error, with description in this application.

"Aminopeptidase polypeptide" or "aminopeptidase protein" refers to the polypeptide in SEQ ID NO 1 or encoded by the deposited cDNA. The term "aminopeptidase protein" or "aminopeptidase polypeptide", however, further includes the numerous variants described herein, as well as fragments derived from the full-length aminopeptidase and variants.

Figure 5:
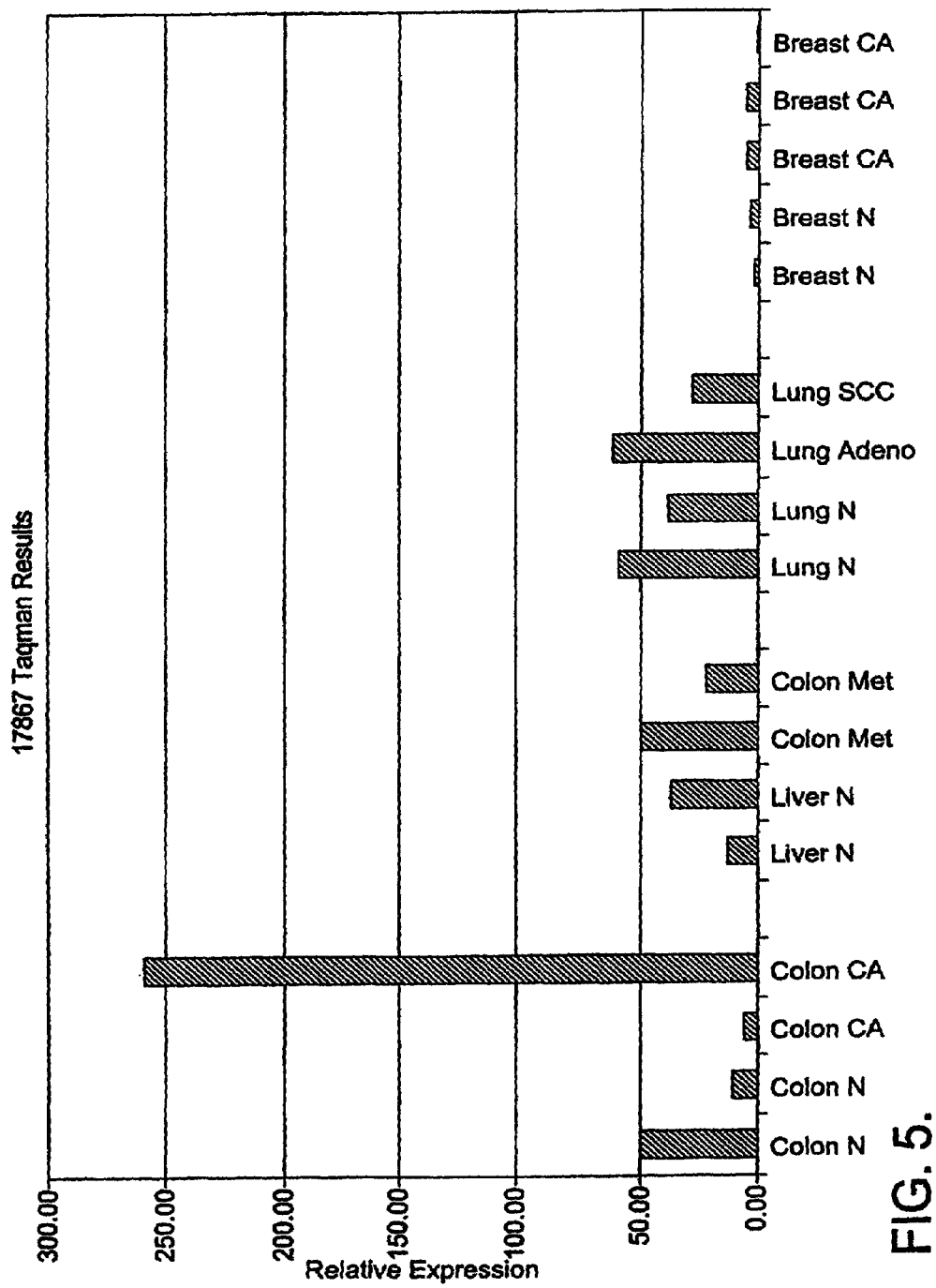
FIG. 5 shows RNA expression of the aminopeptidase in normal human tissues and in carcinomas.
Figure 6:
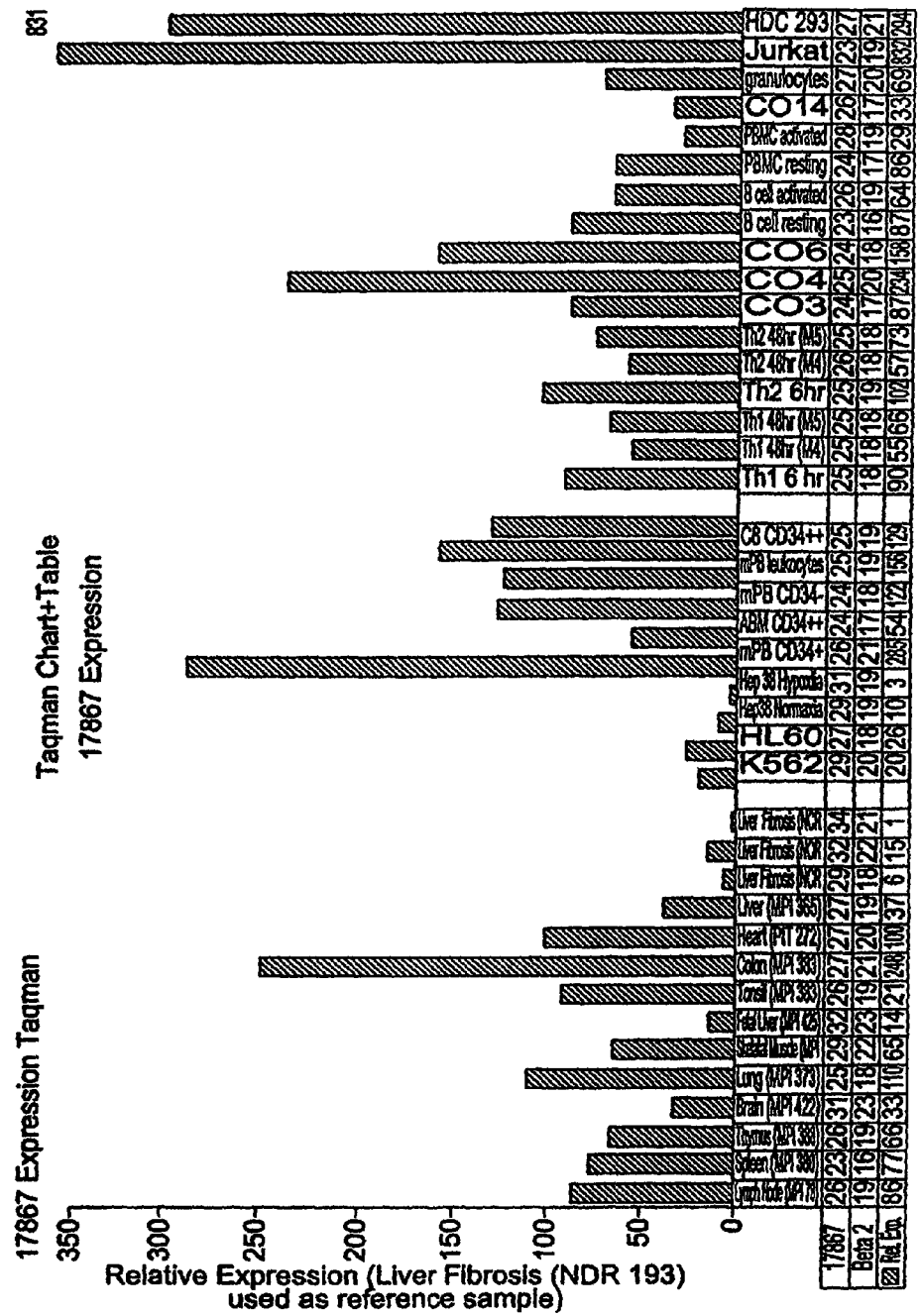
FIG. 6 shows RNA expression of the aminopeptidase in human tissues and cells.

Tissues and/or cells in which the aminopeptidase is found include, but are not limited to, the tissues shown in FIGS. 5 and 6. In addition to these tissues, expression has also been found in colon and breast carcinoma and in lung carcinoma, especially squamous cell carcinoma.

The present invention thus provides an isolated or purified aminopeptidase polypeptide and variants and fragments thereof.

Based on a BLAST search, highest homology was shown to an insulin-regulated membrane aminopeptidase.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The aminopeptidase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the aminopeptidase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

An aminopeptidase polypeptide is also considered to be isolated when it is part of a membrane preparation or is purified and then reconstituted with membrane vesicles or liposomes.

The language "substantially free of chemical precursors or other chemicals" includes preparations of the aminopeptidase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the aminopeptidase polypeptide comprises the amino acid sequence shown in SEQ ID NO 1. However, the invention also encompasses sequence variants. Variants include a substantially homologous protein encoded by the same genetic locus in an organism, i.e., an allelic variant. Variants also encompass proteins derived from other genetic loci in an organism, but having substantial homology to the aminopeptidase of SEQ ID NO 1. Variants also include proteins substantially homologous to the aminopeptidase but derived from another organism, i.e., an ortholog. Variants also include proteins that are substantially homologous to the aminopeptidase that are produced by chemical synthesis. Variants also include proteins that are substantially homologous to the aminopeptidase that are produced by recombinant methods. It is understood, however, that variants exclude any amino acid sequences disclosed prior to the invention.

As used herein, two proteins (or a region of the proteins) are substantially homologous when the amino acid sequences are at least about 60-65%, 65-70%, 70-75%, typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO 2 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the aminopeptidase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873-5877. Such an algorithm is incorporated into the NBLAST and XBLAST programs (version 2.0) as described in Altschul et al. (1997) *Nucleic Acids Res.* 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444-453) algorithm which has been incorporated into the GAP program in the GCG software package
  using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3-5; and FASTA described in Pearson et al. (1988) *PNAS* 85:2444-8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to the catalytic region, regulatory regions, substrate binding regions, zinc binding regions, regions involved in membrane association, and regions involved in enzyme modification, for example, by phosphorylation.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the aminopeptidase polypeptide. This includes preventing immunogenicity from pharmaceutical formulations by preventing protein aggregation.

Useful variations further include alteration of catalytic activity. For example, one embodiment involves a variation at the peptide binding site that results in binding but not hydrolysis of the peptide substrate. A further useful variation at the same site can result in altered affinity for the peptide substrate. Useful variations also include changes that provide for affinity for another peptide substrate. Another useful variation provides a fusion protein in which one or more domains or subregions are operationally fused to one or more domains or subregions from another aminopeptidase.

Amino acids that are essential for function can be identified by methods known in the art, such as site-directed mutagenesis or alanine-scanning mutagenesis (Cunningham et al. (1985) *Science* 244:1081-1085). The latter procedure introduces single alanine mutations at every residue in the molecule. The resulting mutant molecules are then tested for biological activity, such as peptide bond hydrolysis in vitro or related biological activity, such as proliferative activity. Sites that are critical for binding can also be determined by structural analysis such as crystallization, nuclear magnetic resonance or photoaffinity labeling (Smith et al. (1992) *J. Mol. Biol.* 224:899-904; de Vos et al. (1992) *Science* 255:306-312).

Substantial homology can be to the entire nucleic acid or amino acid sequence or to fragments of these sequences.

The invention thus also includes polypeptide fragments of the aminopeptidase. Fragments can be derived from the amino acid sequence shown in SEQ ID NO. 1. However, the invention also encompasses fragments of the variants of the aminopeptidase as described herein.

The fragments to which the invention pertains, however, are not to be construed as encompassing fragments that may be disclosed prior to the present invention.

Accordingly, a fragment can comprise at least about 10, 15, 20, 25, 30, 35, 40, 45, 50 or more contiguous amino acids. Fragments can retain one or more of the biological activities of the protein, for example the ability to bind to or hydrolyze target peptides, as well as fragments that can be used as an immunogen to generate aminopeptidase antibodies.

Biologically active fragments (peptides which are, for example, 5, 7, 10, 12, 15, 20, 30, 35, 36, 37, 38, 39, 40, 50, 100 or more amino acids in length) can comprise a functional site. Such sites include but are not limited to the catalytic site, regulatory sites, sites important for substrate recognition or binding, zinc binding region, the region containing a metalloprotease motif (IAHELAHQW; amino acids 368-376 of SEQ ID NO:1), sites containing the motif characteristic of aminopeptidases in the M1 family (GAMEN; amino acids 334-338 of SEQ ID NO:1), the site contributing to exopeptidase specificity, the peptidase domain from about amino acid 69 to about amino acid 458, phosphorylation sites, glycosylation sites, and other functional sites disclosed herein.

Such sites or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific sites or regions disclosed herein, which sub-fragments retain the function of the site or region from which they are derived.

These regions can be identified by well-known methods involving computerized homology analysis.

The invention also provides fragments with immunogenic properties. These contain an epitope-bearing portion of the aminopeptidase and variants. These epitope-bearing peptides are useful to raise antibodies that bind specifically to an aminopeptidase polypeptide or region or fragment. These peptides can contain at least 10, 12, at least 14, or between at least about 15 to about 30 amino acids.

Figure 2:
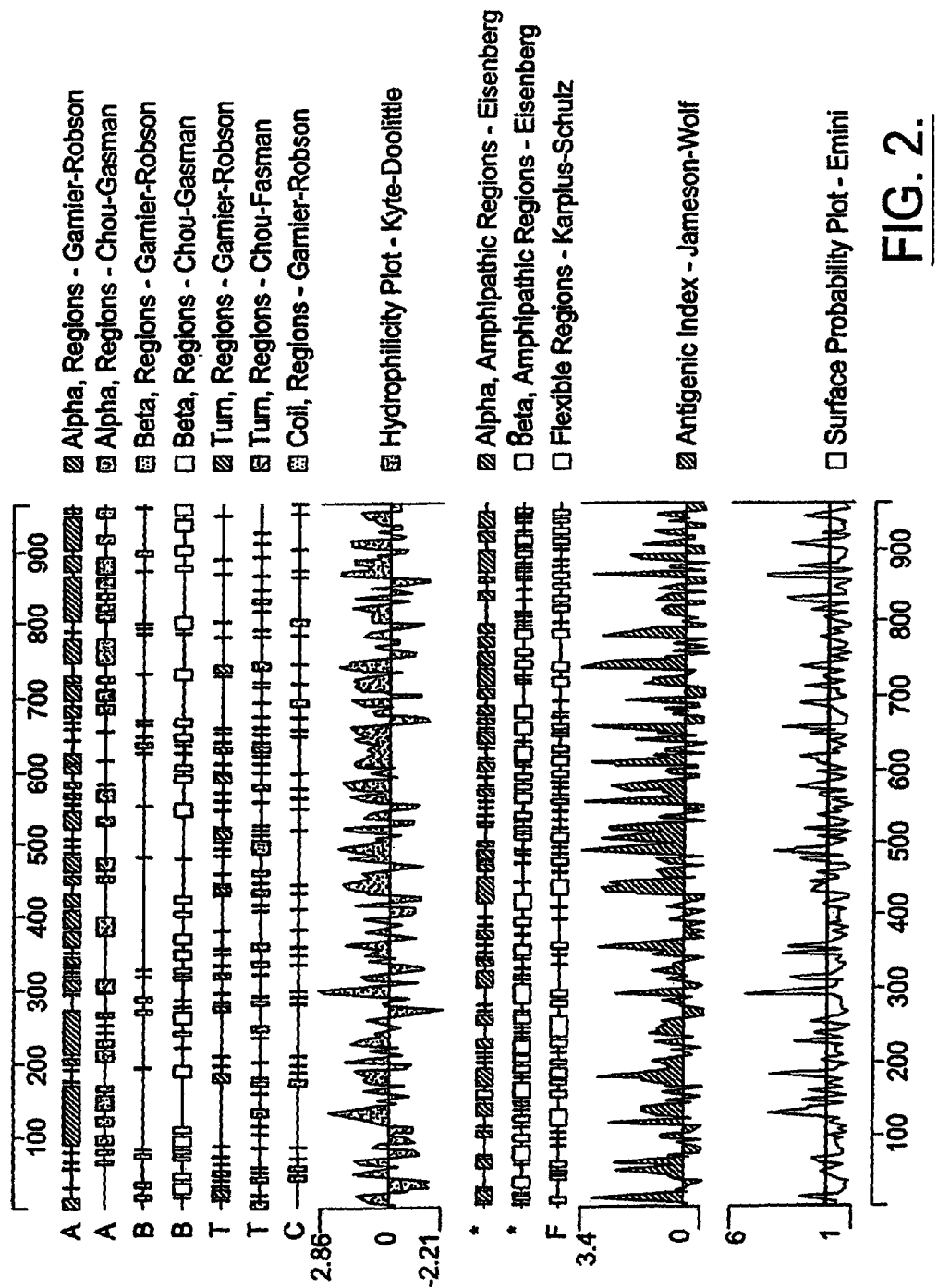
FIG. 2 shows an analysis of the aminopeptidase amino acid sequence: αβturn and coil regions; hydrophilicity; amphipathic regions; flexible regions; antigenic index; and surface probability plot.
Figure 3:
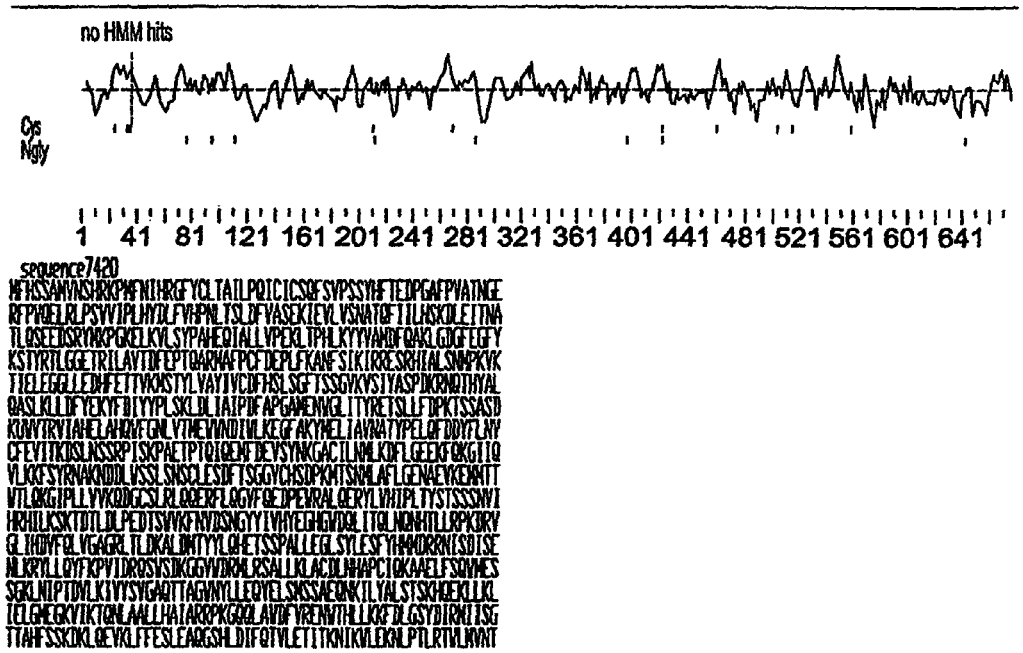
FIG. 3 shows a hydrophobicity plot of the aminopeptidase.

Non-limiting examples of antigenic polypeptides that can be used to generate antibodies include but are not limited to peptides derived from extracellular regions. Regions having a high antigenicity index are shown in FIG. 2. However, intracellularly-made antibodies ("intrabodies") are also encompassed, which would recognize intracellular peptide regions.

The epitope-bearing aminopeptidase polypeptides may be produced by any conventional means (Houghten, R. A. (1985) *Proc. Natl. Acad. Sci. USA* 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the aminopeptidase fragment and an additional region fused to the carboxyl terminus of the fragment.

The invention thus provides chimeric or fusion proteins. These comprise an aminopeptidase peptide sequence operatively linked to a heterologous peptide having an amino acid sequence not substantially homologous to the aminopeptidase. "Operatively linked" indicates that the aminopeptidase peptide and the heterologous peptide are fused in-frame. The heterologous peptide can be fused to the N-terminus or C-terminus of the aminopeptidase or can be internally located.

In one embodiment the fusion protein does not affect aminopeptidase function per se. For example, the fusion protein can be a GST-fusion protein in which the aminopeptidase sequences are fused to the C-terminus of the GST sequences. Other types of fusion proteins include, but are not limited to, enzymatic fusion proteins, for example beta-galactosidase fusions, yeast two-hybrid GAL4 fusions, poly-His fusions and Ig fusions. Such fusion proteins, particularly poly-His fusions, can facilitate the purification of recombinant aminopeptidase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52-58 (1995) and Johanson et al. *J. Biol. Chem.* 270:9459-9471). Thus, this invention also encompasses soluble fusion proteins containing an aminopeptidase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An aminopeptidase-encoding nucleic acid can be cloned into such an expression vector such that the fusion moiety is linked in-frame to the aminopeptidase.

Another form of fusion protein is one that directly affects aminopeptidase functions. Accordingly, an aminopeptidase polypeptide is encompassed by the present invention in which one or more of the aminopeptidase regions (or parts thereof) has been replaced by homologous regions (or parts thereof) from another aminopeptidase. Accordingly, various permutations are possible. Thus, chimeric aminopeptidases can be formed in which one or more of the native domains or subregions has been replaced by another.

Additionally, chimeric aminopeptidase proteins can be produced in which one or more functional sites is derived from a different aminopeptidase. It is understood however that sites could be derived from aminopeptidases that occur in the mammalian genome but which have not yet been discovered or characterized.

The isolated aminopeptidase protein can be purified from cells that naturally express it, such as from any of those tissues shown in FIGS. 5 and 6, especially purified from cells that have been altered to express it (recombinant), or synthesized using known protein synthesis methods.

In one embodiment, the protein is produced by recombinant DNA techniques. For example, a nucleic acid molecule encoding the aminopeptidase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W.H. Freeman and Company, New York (1993). Many detailed reviews are available on this subject, such as by Wold, F., *Posttranslational Covalent Modification of Proteins,* B. C. Johnson, Ed., Academic Press, New York 1-12 (1983); Seifter et al. (1990) *Meth. Enzymol.* 182: 626-646) and Rattan et al. (1992) *Ann. N.Y. Acad. Sci.* 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The aminopeptidase polypeptides are useful for producing antibodies specific for the aminopeptidase, regions, or fragments. Regions having a high antigenicity index score are shown in FIG. 2.

The aminopeptidase polypeptides are useful for biological assays related to aminopeptidases. Such assays involve any of the known aminopeptidase functions or activities or properties useful for diagnosis and treatment of aminopeptidase-related conditions.

The aminopeptidase polypeptides are also useful in drug screening assays, in cell-based or cell-free systems. Cell-based systems can be native, i.e., cells that normally express the aminopeptidase, as a biopsy or expanded in cell culture. In one embodiment, however, cell-based assays involve recombinant host cells expressing the aminopeptidase.

Determining the ability of the test compound to interact with the aminopeptidase can also comprise determining the ability of the test compound to preferentially bind to the polypeptide as compared to the ability of a known binding molecule to bind to the polypeptide.

The polypeptides can be used to identify compounds that modulate aminopeptidase activity. Such compounds, for example, can increase or decrease affinity or rate of binding to peptide substrate, compete with peptide substrate for binding to the aminopeptidase, or displace peptide substrate bound to the aminopeptidase. Both aminopeptidase and appropriate variants and fragments can be used in high-throughput screens to assay candidate compounds for the ability to bind to the aminopeptidase. These compounds can be further screened against a functional aminopeptidase to determine the effect of the compound on the aminopeptidase activity. Compounds can be identified that activate (agonist) or inactivate (antagonist) the aminopeptidase to a desired degree. Modulatory methods can be performed in vitro (e.g., by culturing the cell with the agent) or, alternatively, in vivo (e.g., by administering the agent to a subject).

The aminopeptidase polypeptides can be used to screen a compound for the ability to stimulate or inhibit interaction between the aminopeptidase protein and a target molecule that normally interacts with the aminopeptidase protein, for example, substrate-peptide or zinc component. The assay includes the steps of combining the aminopeptidase protein with a candidate compound under conditions that allow the aminopeptidase protein or fragment to interact with the target molecule, and to detect the formation of a complex between the aminopeptidase protein and the target or to detect the biochemical consequence of the interaction with the aminopeptidase and the target.

Determining the ability of the aminopeptidase to bind to a target molecule can also be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354: 84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble full-length aminopeptidase or fragment that competes for peptide binding. Other candidate compounds include mutant aminopeptidases or appropriate fragments containing mutations that affect aminopeptidase function and compete for peptide substrate. Accordingly, a fragment that competes for substrate, for example with a higher affinity, or a fragment that binds substrate but does not degrade it, is encompassed by the invention.

The invention provides other end points to identify compounds that modulate (stimulate or inhibit) aminopeptidase activity. The assays typically involve an assay of cellular events that indicate aminopeptidase activity. Thus, the expression of genes that are up- or down-regulated in response to the aminopeptidase activity can be assayed. In one embodiment, the regulatory region of such genes can be operably linked to a marker that is easily detectable, such as luciferase. Alternatively, modification of the aminopeptidase could also be measured.

Any of the biological or biochemical functions mediated by the aminopeptidase can be used as an endpoint assay. These include all of the biochemical or biochemical/biological events described herein, in the references cited herein, incorporated by reference for these endpoint assay targets, and other functions known to those of ordinary skill in the art.

In the case of the aminopeptidase, specific end points can include peptide bond hydrolysis.

Binding and/or activating compounds can also be screened by using chimeric aminopeptidase proteins in which one or more regions, segments, sites, and the like, as disclosed herein, or parts thereof, can be replaced by their heterologous counterparts derived from other aminopeptidases. For example, a catalytic region can be used that interacts with a different peptide sequence specificity and/or affinity than the native aminopeptidase. Accordingly, a different set of components is available as an end-point assay for activation. As a further alternative, the site of modification by an effector protein, for example phosphorylation, can be replaced with the site for a different effector protein. Activation can also be detected by a reporter gene containing an easily detectable coding region operably linked to a transcriptional regulatory sequence that is part of the native pathway in which the aminopeptidase is involved.

The aminopeptidase polypeptides are also useful in competition binding assays in methods designed to discover compounds that interact with the aminopeptidase. Thus, a compound is exposed to an aminopeptidase polypeptide under conditions that allow the compound to bind or to otherwise interact with the polypeptide. Soluble aminopeptidase polypeptide is also added to the mixture. If the test compound interacts with the soluble aminopeptidase polypeptide, it decreases the amount of complex formed or activity from the aminopeptidase target. This type of assay is particularly useful in cases in which compounds are sought that interact with specific regions of the aminopeptidase. Thus, the soluble polypeptide that competes with the target aminopeptidase region is designed to contain peptide sequences corresponding to the region of interest.

Another type of competition-binding assay can be used to discover compounds that interact with specific functional sites. As an example, bindable zinc and a candidate compound can be added to a sample of the aminopeptidase. Compounds that interact with the aminopeptidase at the same site as the zinc will reduce the amount of complex formed between the aminopeptidase and the zinc. Accordingly, it is possible to discover a compound that specifically prevents interaction between the aminopeptidase and the zinc component. Another example involves adding a candidate compound to a sample of aminopeptidase and substrate peptide. A compound that competes with the peptide will reduce the amount of hydrolysis or binding of the peptide to the aminopeptidase. Accordingly, compounds can be discovered that directly interact with the aminopeptidase and compete with the peptide. Such assays can involve any other component that interacts with the aminopeptidase.

To perform cell free drug screening assays, it is desirable to immobilize either the aminopeptidase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/aminopeptidase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of aminopeptidase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of an aminopeptidase-binding target component, such as a peptide or zinc component, and a candidate compound are incubated in the aminopeptidase-presenting wells and the amount of complex trapped in the well can be quantitated. Methods for detecting such complexes, in addition to those described above for the GST-immobilized complexes, include immunodetection of complexes using antibodies reactive with the aminopeptidase target molecule, or which are reactive with aminopeptidase and compete with the target molecule; as well as enzyme-linked assays which rely on detecting an enzymatic activity associated with the target molecule.

Modulators of aminopeptidase activity identified according to these drug screening assays can be used to treat a subject with a disorder related to the aminopeptidase, by treating cells that express the aminopeptidase, such as any of those shown in FIGS. 5 and 6. These methods of treatment include the steps of administering the modulators of aminopeptidase activity in a pharmaceutical composition as described herein, to a subject in need of such treatment.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconiosis, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders in which aminopeptidase expression is especially relevant include, but are not limited to, breast and colon carcinoma, lung carcinoma, especially squamous cell carcinoma, and insulin related disorders such as diabetes.

The aminopeptidase is overexpressed in both lung, breast, and colon cancer. As such, the gene is particularly relevant for the treatment of these disorders, where inhibiting expression of the gene could affect tumor development and/or progression.

The aminopeptidase is also expressed in the tissues shown in FIGS. 5 and 6, and as such is specifically involved in disorders relating to these tissues.

The aminopeptidase polypeptides are thus useful for treating an aminopeptidase-associated disorder characterized by aberrant expression or activity of an aminopeptidase. In one embodiment, the method involves administering an agent (e.g., an agent identified by a screening assay described herein), or combination of agents that modulates (e.g., upregulates or downregulates) expression or activity of the protein. In another embodiment, the method involves administering the aminopeptidase as therapy to compensate for reduced or aberrant expression or activity of the protein.

Methods for treatment include but are not limited to the use of soluble aminopeptidase or fragments of the aminopeptidase protein that compete for substrate or any other component that directly interacts with the aminopeptidase, such as zinc or any of the enzymes that modify the aminopeptidase. These aminopeptidases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO 94/10300), to identify other proteins (captured proteins) which bind to or interact with the proteins of the invention and modulate their activity.

The aminopeptidase polypeptides also are useful to provide a target for diagnosing a disease or predisposition to disease mediated by the aminopeptidase, including, but not limited to, those diseases discussed herein, and particularly lung, breast, and colon carcinoma and insulin-related disorders, such as diabetes. Targets are useful for diagnosing a disease or predisposition to disease mediated by the aminopeptidase, in the tissues shown in FIGS. 5 and 6. Accordingly, methods are provided for detecting the presence, or levels of, the aminopeptidase in a cell, tissue, or organism. The method involves contacting a biological sample with a compound capable of interacting with the aminopeptidase such that the interaction can be detected.

One agent for detecting aminopeptidase is an antibody capable of selectively binding to aminopeptidase. A biological sample includes tissues, cells and biological fluids isolated from a subject, as well as tissues, cells and fluids present within a subject.

The aminopeptidase also provides a target for diagnosing active disease, or predisposition to disease, in a patient having a variant aminopeptidase. Thus, aminopeptidase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered aminopeptidase activity in cell-based or cell-free assay, alteration in peptide binding or degradation, zinc binding or antibody-binding pattern, altered isoelectric point, direct amino acid sequencing, and any other of the known assay techniques useful for detecting mutations in a protein in general or in an aminopeptidase specifically.

In vitro techniques for detection of aminopeptidase include enzyme linked immunosorbent assays (ELISAs), Western blots, immunoprecipitations and immunofluorescence. Alternatively, the protein can be detected in vivo in a subject by introducing into the subject a labeled anti-aminopeptidase antibody. For example, the antibody can be labeled with a radioactive marker whose presence and location in a subject can be detected by standard imaging techniques. Particularly useful are methods, which detect the allelic variant of the aminopeptidase expressed in a subject, and methods, which detect fragments of the aminopeptidase in a sample.

The aminopeptidase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10-11):983-985, and Linder, M. W. (1997) Clin. Chem. 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the aminopeptidase in which one or more of the aminopeptidase functions in one population is different from those in another population. The polypeptides thus allow a target to ascertain a genetic predisposition that can affect treatment modality. Thus, in a peptide-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The aminopeptidase polypeptides are also useful for monitoring therapeutic effects during clinical trials and other treatment. Thus, the therapeutic effectiveness of an agent that is designed to increase or decrease gene expression, protein levels or aminopeptidase activity can be monitored over the course of treatment using the aminopeptidase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein

Antibodies

The invention also provides antibodies that selectively bind to the aminopeptidase and its variants and fragments. An antibody is considered to selectively bind, even if it also binds to other proteins that are not substantially homologous with the aminopeptidase. These other proteins share homology with a fragment or domain of the aminopeptidase. This conservation in specific regions gives rise to antibodies that bind to both proteins by virtue of the homologous sequence. In this case, it would be understood that antibody binding to the aminopeptidase is still selective.

To generate antibodies, an isolated aminopeptidase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 2.

Antibodies are preferably prepared from these regions or from discrete fragments in these regions. However, antibodies can be prepared from any region of the peptide as described herein. A preferred fragment produces an antibody that diminishes or completely prevents peptide hydrolysis or binding. Antibodies can be developed against the entire aminopeptidase or domains of the aminopeptidase as described herein, for example, the zinc binding region, metalloprotease motif (IAHELAHQW; amino acids 368-376 of SEQ ID NO:1), the GAMEN motif (amino acids 334-338 of SEQ ID NO:1), sites contributing to exopeptidase specificity, and the peptidase domain or subregions thereof. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab') 2) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Antibody Uses

The antibodies can be used to isolate an aminopeptidase by standard techniques, such as affinity chromatography or immunoprecipitation. The antibodies can facilitate the purification of the natural aminopeptidase from cells and recombinantly produced aminopeptidase expressed in host cells.

The antibodies are useful to detect the presence of aminopeptidase in cells or tissues to determine the pattern of expression of the aminopeptidase among various tissues in an organism and over the course of normal development.

The antibodies can be used to detect aminopeptidase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length aminopeptidase can be used to identify aminopeptidase turnover.

Further, the antibodies can be used to assess aminopeptidase expression in disease states such as in active stages of the disease or in an individual with a predisposition toward disease related to aminopeptidase function. When a disorder is caused by an inappropriate tissue distribution, developmental expression, or level of expression of the aminopeptidase protein, the antibody can be prepared against the normal aminopeptidase protein. If a disorder is characterized by a specific mutation in the aminopeptidase, antibodies specific for this mutant protein can be used to assay for the presence of the specific mutant aminopeptidase. However, intracellularly-made antibodies ("intrabodies") are also encompassed, which would recognize intracellular aminopeptidase peptide regions.

The antibodies can also be used to assess normal and aberrant subcellular localization of cells in the various tissues in an organism. Antibodies can be developed against the whole aminopeptidase or portions of the aminopeptidase, for example, portions of the peptidase domain from amino acids 69-458 of SEQ ID NO:1, including substrate recognition site.

The diagnostic uses can be applied, not only in genetic testing, but also in monitoring a treatment modality. Accordingly, where treatment is ultimately aimed at correcting aminopeptidase expression level or the presence of aberrant aminopeptidases and aberrant tissue distribution or developmental expression, antibodies directed against the aminopeptidase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic aminopeptidase can be used to identify individuals that require modified treatment modalities.

The antibodies are also useful as diagnostic tools as an immunological marker for aberrant aminopeptidase analyzed by electrophoretic mobility, isoelectric point, tryptic peptide digest, and other physical assays known to those in the art.

The antibodies are also useful for tissue typing. Thus, where a specific aminopeptidase has been correlated with expression in a specific tissue, antibodies that are specific for this aminopeptidase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting aminopeptidase function, for example, zinc binding, and peptide binding and/or hydrolysis.

These uses can also be applied in a therapeutic context in which treatment involves inhibiting aminopeptidase function. An antibody can be used, for example, to block peptide binding. Antibodies can be prepared against specific fragments containing sites required for function or against intact aminopeptidase associated with a cell.

Completely human antibodies are particularly desirable for therapeutic treatment of human patients. For an overview of this technology for producing human antibodies, see Lonberg et al. (1995) *Int. Rev. Immunol.* 13:65-93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of an aminopeptidase protein in a biological sample. The kit can comprise antibodies such as a labeled or labelable antibody and a compound or agent for detecting aminopeptidase in a biological sample; means for determining the amount of aminopeptidase in the sample; and means for comparing the amount of aminopeptidase in the sample with a standard. The compound or agent can be packaged in a suitable container. The kit can further comprise instructions for using the kit to detect aminopeptidase.

Polynucleotides

The nucleotide sequence in SEQ ID NO 2 was obtained by sequencing the deposited human cDNA. Accordingly, the sequence of the deposited clone is controlling as to any discrepancies between the two and any reference to the sequence of SEQ ID NO 2 includes reference to the sequence of the deposited cDNA.

The specifically disclosed cDNA comprises the coding region and 5' and 3' untranslated sequences in SEQ ID NO 2.

The invention provides isolated polynucleotides encoding the novel aminopeptidase. The term "aminopeptidase polynucleotide" or "aminopeptidase nucleic acid" refers to the sequence shown in SEQ ID NO 2 or in the deposited cDNA. The term "aminopeptidase polynucleotide" or "aminopeptidase nucleic acid" further includes variants and fragments of the aminopeptidase polynucleotides.

An "isolated" aminopeptidase nucleic acid is one that is separated from other nucleic acid present in the natural source of the aminopeptidase nucleic acid. Preferably, an "isolated" nucleic acid is free of sequences which naturally flank the aminopeptidase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the aminopeptidase nucleic acid is isolated from flanking sequences such that it can be subjected to the specific manipulations described herein, such as recombinant expression, preparation of probes and primers, and other uses specific to the aminopeptidase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The aminopeptidase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The aminopeptidase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Aminopeptidase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

Aminopeptidase nucleic acid can comprise the nucleotide sequences shown in SEQ ID NO 2, corresponding to human endothelial cell cDNA In one embodiment, the aminopeptidase nucleic acid comprises only the coding region.

The invention further provides variant aminopeptidase polynucleotides, and fragments thereof, that differ from the nucleotide sequence shown in SEQ ID NO 2 due to degeneracy of the genetic code and thus encode the same protein as that encoded by the nucleotide sequence shown in SEQ ID NO 2.

The invention also provides aminopeptidase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NO 2 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding an aminopeptidase that is typically at least about 60-65%, 65-70%, 70-75%, more typically at least about 80-85%, and most typically at least about 90-95% or more homologous to the nucleotide sequence shown in SEQ ID NO 2 or a fragment of this sequence. Such nucleic acid molecules can readily be identified as being able to hybridize under stringent conditions, to the nucleotide sequence shown in SEQ ID NO 2 or a fragment of the sequence. It is understood that stringent hybridization does not indicate substantial homology where it is due to general homology, such as poly A sequences, or sequences common to all or most proteins, metalloproteases, all zinc binding proteins, all proteins in the M1 family, or all aminopeptidases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least 50-55%, 55% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2×SSC/0.1% SDS at room temperature, or by one or more moderate stringency washes in 0.2× SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO 2 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS.

Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO 2 or the complement of SEQ ID NO 2. In one embodiment, the nucleic acid consists of a portion of the nucleotide sequence of SEQ ID NO 2 and the complement of SEQ ID NO 2. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length aminopeptidase polynucleotides. The fragment can be single or double-stranded and can comprise DNA or RNA. The fragment can be derived from either the coding or the non-coding sequence.

In another embodiment an isolated aminopeptidase nucleic acid encodes the entire coding region. In another embodiment the isolated aminopeptidase nucleic acid encodes a sequence corresponding to the mature protein that may be from about amino acid 6 to the last amino acid. Other fragments include nucleotide sequences encoding the amino acid fragments described herein.

Thus, aminopeptidase nucleic acid fragments further include sequences corresponding to the regions described herein, subregions also described, and specific functional sites. Aminopeptidase nucleic acid fragments also include combinations of the regions, segments, motifs, and other functional sites described above. A person of ordinary skill in the art would be aware of the many permutations that are possible.

Where the location of the regions or sites have been predicted by computer analysis, one of ordinary sill would appreciate that the amino acid residues constituting these regions can vary depending on the criteria used to define the regions.

However, it is understood that an aminopeptidase fragment includes any nucleic acid sequence that does not include the entire gene.

The invention also provides aminopeptidase nucleic acid fragments that encode epitope bearing regions of the aminopeptidase proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17): 3389-3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO 2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The aminopeptidase polynucleotides are thus useful for probes, primers, and in biological assays.

Where the polynucleotides are used to assess aminopeptidase properties or functions, such as in the assays described herein, all or less than all of the entire cDNA can be useful. Assays specifically directed to aminopeptidase functions, such as assessing agonist or antagonist activity, encompass the use of known fragments. Further, diagnostic methods for assessing aminopeptidase function can also be practiced with any fragment, including those fragments that may have been known prior to the invention. Similarly, in methods involving treatment of aminopeptidase dysfunction, all fragments are encompassed including those, which may have been known in the art.

The aminopeptidase polynucleotides are useful as a hybridization probe for cDNA and genomic DNA to isolate a full-length cDNA and genomic clones encoding the polypeptides described in SEQ ID NO 1 and to isolate cDNA and genomic clones that correspond to variants producing the same polypeptides shown in SEQ ID NO 1 or the other variants described herein. Variants can be isolated from the same tissue and organism from which the polypeptides shown in SEQ ID NO 1 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the aminopeptidase. Accordingly, it could be derived from 5' noncoding regions, the coding region, and 3' noncoding regions.

The nucleic acid probe can be, for example, the full-length cDNA of SEQ ID NO 2, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO 2, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell aminopeptidases in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The aminopeptidase polynucleotides are also useful as primers for PCR to amplify any given region of an aminopeptidase polynucleotide.

The aminopeptidase polynucleotides are also useful for constructing recombinant vectors. Such vectors include expression vectors that express a portion of, or all of, the aminopeptidase polypeptides. Vectors also include insertion vectors, used to integrate into another polynucleotide sequence, such as into the cellular genome, to alter in situ expression of aminopeptidase genes and gene products. For example, an endogenous aminopeptidase coding sequence can be replaced via homologous recombination with all or part of the coding region containing one or more specifically introduced mutations.

The aminopeptidase polynucleotides are also useful for expressing antigenic portions of the aminopeptidase proteins.

The aminopeptidase polynucleotides are also useful as probes for determining the chromosomal positions of the aminopeptidase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The aminopeptidase polynucleotide probes are also useful to determine patterns of the presence of the gene encoding the aminopeptidases and their variants with respect to tissue distribution, for example, whether gene duplication has occurred and whether the duplication occurs in all or only a subset of tissues. The genes can be naturally occurring or can have been introduced into a cell, tissue, or organism exogenously.

The aminopeptidase polynucleotides are also useful for designing ribozymes corresponding to all, or a part, of the mRNA produced from genes encoding the polynucleotides described herein.

The aminopeptidase polynucleotides are also useful for constructing host cells expressing a part, or all, of the aminopeptidase polynucleotides and polypeptides.

The aminopeptidase polynucleotides are also useful for constructing transgenic animals expressing all, or a part, of the aminopeptidase polynucleotides and polypeptides.

The aminopeptidase polynucleotides are also useful for making vectors that express part, or all, of the aminopeptidase polypeptides.

The aminopeptidase polynucleotides are also useful as hybridization probes for determining the level of aminopeptidase nucleic acid expression. Accordingly, the probes can be used to detect the presence of, or to determine levels of, aminopeptidase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the aminopeptidase genes.

Alternatively, the probe can be used in an in situ hybridization context to assess the position of extra copies of the aminopeptidase genes, as on extrachromosomal elements or as integrated into chromosomes in which the aminopeptidase gene is not normally found, for example as a homogeneously staining region.

These uses are relevant for diagnosis of disorders involving an increase or decrease in aminopeptidase expression relative to normal, such as a proliferative disorder, a differentiative or developmental disorder, or a hematopoietic disorder.

Disorders in which the aminopeptidase expression is relevant include, but are not limited to, lung and colon carcinomas and insulin-related disorders, such as diabetes.

The aminopeptidase is expressed in the tissues shown in FIGS. 5 and 6. As such, the gene is particularly relevant for the treatment of disorders involving these tissues, especially lung, breast, and colon.

Thus, the present invention provides a method for identifying a disease or disorder associated with aberrant expression or activity of aminopeptidase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity.

Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the aminopeptidase, such as by measuring the level of an aminopeptidase-encoding nucleic acid in a sample of cells from a subject e.g., mRNA or genomic DNA, or determining if the aminopeptidase gene has been mutated.

Nucleic acid expression assays are useful for drug screening to identify compounds that modulate aminopeptidase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the aminopeptidase gene. The method typically includes assaying the ability of the compound to modulate the expression of the aminopeptidase nucleic acid and thus identifying a compound that can be used to treat a disorder characterized by undesired aminopeptidase nucleic acid expression.

The assays can be performed in cell-based and cell-free systems. Cell-based assays include cells naturally expressing the aminopeptidase nucleic acid or recombinant cells genetically engineered to express specific nucleic acid sequences.

Alternatively, candidate compounds can be assayed in vivo in patients or in transgenic animals.

The assay for aminopeptidase nucleic acid expression can involve direct assay of nucleic acid levels, such as mRNA levels, or on collateral compounds (such as peptide hydrolysis). Further, the expression of genes that are up- or down-regulated in response to the aminopeptidase activity can also be assayed. In this embodiment the regulatory regions of these genes can be operably linked to a reporter gene such as luciferase.

Thus, modulators of aminopeptidase gene expression can be identified in a method wherein a cell is contacted with a candidate compound and the expression of mRNA determined. The level of expression of aminopeptidase mRNA in the presence of the candidate compound is compared to the level of expression of aminopeptidase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate aminopeptidase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Disorders in which the aminopeptidase expression is relevant include, but are not limited to, those discussed herein and particularly in lung and colon carcinoma and insulin-related disorder, such as diabetes.

Alternatively, a modulator for aminopeptidase nucleic acid expression can be a small molecule or drug identified using the screening assays described herein as long as the drug or small molecule inhibits the aminopeptidase nucleic acid expression.

The aminopeptidase polynucleotides are also useful for monitoring the effectiveness of modulating compounds on the expression or activity of the aminopeptidase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The aminopeptidase polynucleotides are also useful in diagnostic assays for qualitative changes in aminopeptidase nucleic acid, and particularly in qualitative changes that lead to pathology. The polynucleotides can be used to detect mutations in aminopeptidase genes and gene expression products such as mRNA. The polynucleotides can be used as hybridization probes to detect naturally-occurring genetic mutations in the aminopeptidase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the aminopeptidase gene associated with a dysfunction provides a diagnostic tool for an active disease or susceptibility to disease when the disease results from overexpression, underexpression, or altered expression of an aminopeptidase.

Mutations in the aminopeptidase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for detecting point mutations in the gene (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an aminopeptidase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant aminopeptidase gene and a wild-type gene can be determined by direct DNA sequencing. A variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the gene include methods in which protection from cleavage agents is used to detect mismatched bases in RNA/RNA or RNA/DNA duplexes (Myers et al. (1985) Science 230:1242); Cotton et al. (1988) PNAS 85:4397; Saleeba et al. (1992) Meth. Enzymol. 217:286-295), electrophoretic mobility of mutant and wild type nucleic acid is compared (Orita et al. (1989) PNAS 86:2766; Cotton et al. (1993) Mutat. Res. 285:125-144; and Hayashi et al. (1992) Genet. Anal. Tech. Appl. 9:73-79), and movement of mutant or wild-type fragments in polyacrylamide gels containing a gradient of denaturant is assayed using denaturing gradient gel electrophoresis (Myers et al. (1985) Nature 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) Trends Genet. 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) Human Mutation 7:244-255; Kozal et al. (1996) Nature Medicine 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The aminopeptidase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the aminopeptidase gene that results in altered affinity for zinc could result in an excessive or decreased drug effect with standard concentrations of zinc. Accordingly, the aminopeptidase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The aminopeptidase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The aminopeptidase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the aminopeptidase sequence can be used to provide an alternative technique, which determines the actual DNA sequence of selected fragments in the genome of an individual. Thus, the aminopeptidase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The aminopeptidase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The aminopeptidase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The aminopeptidase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The aminopeptidase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of aminopeptidase probes can be used to identify tissue by species and/or by organ type.

In a similar fashion, these primers and probes can be used to screen tissue culture for contamination (i.e. screen for the presence of a mixture of different types of cells in a culture).

Alternatively, the aminopeptidase polynucleotides can be used directly to block transcription or translation of aminopeptidase gene sequences by means of antisense or ribozyme constructs. Thus, in a disorder characterized by abnormally high or undesirable aminopeptidase gene expression, nucleic acids can be directly used for treatment.

The aminopeptidase polynucleotides are thus useful as antisense constructs to control aminopeptidase gene expression in cells, tissues, and organisms. A DNA antisense polynucleotide is designed to be complementary to a region of the gene involved in transcription, preventing transcription and hence production of aminopeptidase protein. An antisense RNA or DNA polynucleotide would hybridize to the mRNA and thus block translation of mRNA into aminopeptidase protein.

Examples of antisense molecules useful to inhibit nucleic acid expression include antisense molecules complementary to a fragment of the 5' untranslated region of SEQ ID NO 2 which also includes the start codon and antisense molecules which are complementary to a fragment of the 3' untranslated region of SEQ ID NO 2.

Alternatively, a class of antisense molecules can be used to inactivate mRNA in order to decrease expression of aminopeptidase nucleic acid. Accordingly, these molecules can treat a disorder characterized by abnormal or undesired aminopeptidase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the aminopeptidase protein.

The aminopeptidase polynucleotides also provide vectors for gene therapy in patients containing cells that are aberrant in aminopeptidase gene expression. Thus, recombinant cells, which include the patient's cells that have been engineered ex vivo and returned to the patient, are introduced into an individual where the cells produce the desired aminopeptidase protein to treat the individual.

The invention also encompasses kits for detecting the presence of an aminopeptidase nucleic acid in a biological sample. For example, the kit can comprise reagents such as a labeled or labelable nucleic acid or agent capable of detecting aminopeptidase nucleic acid in a biological sample; means for determining the amount of aminopeptidase nucleic acid in the sample; and means for comparing the amount of aminopeptidase nucleic acid in the sample with a standard. The compound or agent can be packaged in a suitable container. The kit can further comprise instructions for using the kit to detect aminopeptidase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif" or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the aminopeptidase polynucleotides. The term "vector" refers to a vehicle, preferably a nucleic acid molecule that can transport the aminopeptidase polynucleotides. When the vector is a nucleic acid molecule, the aminopeptidase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the aminopeptidase polynucleotides. Alternatively, the vector may integrate into the host cell genome and produce additional copies of the aminopeptidase polynucleotides when the host cell replicates.

The invention provides vectors for the maintenance (cloning vectors) or vectors for expression (expression vectors) of the aminopeptidase polynucleotides. The vectors can function in procaryotic or eukaryotic cells or in both (shuttle vectors).

Expression vectors contain cis-acting regulatory regions that are operably linked in the vector to the aminopeptidase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the aminopeptidase polynucleotides from the vector. Alternatively, a trans-acting factor may be supplied by the host cell. Finally, a trans-acting factor can be produced from the vector itself.

It is understood, however, that in some embodiments, transcription and/or translation of the aminopeptidase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

A variety of expression vectors can be used to express an aminopeptidase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual* 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The aminopeptidase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the aminopeptidase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119-128). Alternatively, the sequence of the polynucleotide of interest can be altered to provide preferential codon usage for a specific host cell, for example *E. coli*. (Wada et al. (1992) *Nucleic Acids Res.* 20:2111-2118).

The aminopeptidase polynucleotides can also be expressed by expression vectors that are operative in yeast. Examples of vectors for expression in yeast e.g., *S. cerevisiae* include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), and pYES2 (Invitrogen Corporation, San Diego, Calif.).

The aminopeptidase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187-195).

The expression vectors listed herein are provided by way of example only of the well-known vectors available to those of ordinary skill in the art that would be useful to express the aminopeptidase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed., Cold Spring Harbor Laboratory*, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual,* 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the aminopeptidase polynucleotides can be introduced either alone or with other polynucleotides that are not related to the aminopeptidase polynucleotides such as those providing trans-acting factors for expression vectors. When more than one vector is introduced into a cell, the vectors can be introduced independently, co-introduced or joined to the aminopeptidase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the aminopeptidase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing aminopeptidase proteins or polypeptides that can be further purified to produce desired amounts of aminopeptidase protein or fragments. Thus, host cells containing expression vectors are useful for polypeptide production.

Host cells are also useful for conducting cell-based assays involving the aminopeptidase or aminopeptidase fragments. Thus, a recombinant host cell expressing a native aminopeptidase is useful to assay for compounds that stimulate or inhibit aminopeptidase function. This includes zinc or peptide binding, gene expression at the level of transcription or translation, and interaction with other cellular components.

Host cells are also useful for identifying aminopeptidase mutants in which these functions are affected. If the mutants naturally occur and give rise to a pathology, host cells containing the mutations are useful to assay compounds that have a desired effect on the mutant aminopeptidase (for example, stimulating or inhibiting function) which may not be indicated by their effect on the native aminopeptidase.

Recombinant host cells are also useful for expressing the chimeric polypeptides described herein to assess compounds that activate or suppress activation by means of a heterologous domain, segment, site, and the like, as disclosed herein.

Further, mutant aminopeptidases can be designed in which one or more of the various functions is engineered to be increased or decreased and used to augment or replace aminopeptidase proteins in an individual. Thus, host cells can provide a therapeutic benefit by replacing an aberrant aminopeptidase or providing an aberrant aminopeptidase that provides a therapeutic result. In one embodiment, the cells provide aminopeptidases that are abnormally active.

In another embodiment, the cells provide aminopeptidases that are abnormally inactive. These aminopeptidases can compete with endogenous aminopeptidases in the individual.

In another embodiment, cells expressing aminopeptidases that cannot be activated, are introduced into an individual in order to compete with endogenous aminopeptidases for zinc or peptide. For example, in the case in which excessive zinc is part of a treatment modality, it may be necessary to effectively inactivate zinc at a specific point in treatment. Providing cells that compete for the molecule, but which cannot be affected by aminopeptidase activation would be beneficial.

Homologously recombinant host cells can also be produced that allow the in situ alteration of endogenous aminopeptidase polynucleotide sequences in a host cell genome. This technology is more fully described in WO 93/09222, WO 91/12650 and U.S. Pat. No. 5,641,670. Briefly, specific polynucleotide sequences corresponding to the aminopeptidase polynucleotides or sequences proximal or distal to an aminopeptidase gene are allowed to integrate into a host cell genome by homologous recombination where expression of the gene can be affected. In one embodiment, regulatory sequences are introduced that either increase or decrease expression of an endogenous sequence. Accordingly, an aminopeptidase protein can be produced in a cell not normally producing it, or increased expression of aminopeptidase protein can result in a cell normally producing the protein at a specific level. Alternatively, the entire gene can be deleted. Still further, specific mutations can be introduced into any desired region of the gene to produce mutant aminopeptidase proteins. Such mutations could be introduced, for example, into the specific regions disclosed herein.

In one embodiment, the host cell can be a fertilized oocyte or embryonic stem cell that can be used to produce a transgenic animal containing the altered aminopeptidase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous aminopeptidase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an aminopeptidase protein and identifying and evaluating modulators of aminopeptidase protein activity.

Other examples of transgenic animals include non-human primates, sheep, dogs, cows, goats, chickens, and amphibians.

In one embodiment, a host cell is a fertilized oocyte or an embryonic stem cell into which aminopeptidase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the aminopeptidase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the aminopeptidase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding or activation, may not be evident from in vitro cell-free or cell-based assays. Accordingly, it is useful to provide non-human transgenic animals to assay in vivo aminopeptidase function, including peptide interaction, the effect of specific mutant aminopeptidases on aminopeptidase function and peptide interaction, and the effect of chimeric aminopeptidases. It is also possible to assess the effect of null mutations, that is mutations that substantially or completely eliminate one or more aminopeptidase functions.

Pharmaceutical Compositions

The aminopeptidase nucleic acid molecules, protein, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo by in vivo transcription or translation of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an aminopeptidase protein or anti-aminopeptidase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328, 470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

The invention claimed is:

1. A method for identifying a compound which binds to a polypeptide, comprising:
   (a) contacting:
      (i) a polypeptide; or
      (ii) a cell expressing the polypeptide
   with a test compound; and
   (b) determining whether the polypeptide binds to the test compound, wherein the polypeptide is selected from the group consisting of:
      (1) a polypeptide comprising an amino acid sequence which is at least 95% identical to the amino acid sequence of SEQ ID NO:1;
      (2) a polypeptide which is encoded by a nucleic acid molecule comprising a nucleotide sequence which is at least 90% identical to a nucleic acid comprising the nucleotide sequence of SEQ ID NO:2, SEQ ID NO:3, or the nucleotide sequence of the DNA insert of the plasmid deposited with ATCC as Accession Number PTA-1642; and
      (3) a polypeptide comprising at least 100 contiguous amino acids of the sequence set forth in SEQ ID NO:1.

2. The method of claim 1 wherein the binding of the test compound is detected directly.

3. The method of claim 1 wherein the binding of the test compound is detected using a competition binding assay.

4. The method of claim 1 wherein the binding of the test compound is detected using an assay for aminopeptidase activity.

5. The method of claim 1 wherein the polypeptide comprises an amino acid sequence which is at least 95% identical to the amino acid sequence of SEQ ID NO:1.

6. The method of claim 1 wherein the polypeptide is encoded by a nucleic acid molecule comprising a nucleotide sequence which is at least 90% identical to a nucleic acid comprising the nucleotide sequence of SEQ ID NO:2, SEQ ID NO:3, or the nucleotide sequence of the DNA insert of the plasmid deposited with ATCC as Accession Number PTA-1642.

7. The method of claim 1 wherein the polypeptide comprises at least 100 contiguous amino acids of the sequence set forth in SEQ ID NO:1.

8. The method of claim 1 wherein the polypeptide comprises the amino acid sequence of SEQ ID NO:1.

9. The method of claim 1 wherein the polypeptide is encoded by a nucleic acid molecule comprising the nucleotide sequence of SEQ ID NO:2.

10. The method of claim 1 wherein the polypeptide is encoded by a nucleic acid molecule comprising the nucleotide sequence of SEQ ID NO:3.

11. The method of claim 1 wherein the polypeptide is encoded by a nucleic acid molecule comprising the nucleotide sequence of the DNA insert of the plasmid deposited with ATCC as Accession Number PTA-1642.

12. The method of claim 1 wherein the polypeptide further comprises heterologous amino acid sequences.

13. A method for identifying a compound which modulates the activity of a polypeptide, comprising:
(a) assaying a polypeptide for aminopeptidase activity; and, if aminopeptidase activity is detected,
(b) contacting the polypeptide with a test compound; and
(c) determining an effect of the test compound on the aminopeptidase activity of the polypeptide, wherein the polypeptide is selected from the group consisting of:
  (1) a polypeptide comprising an amino acid sequence which is at least 95% identical to the amino acid sequence of SEQ ID NO:1;
  (2) a polypeptide which is encoded by a nucleic acid molecule comprising a nucleotide sequence which is at least 90% identical to a nucleic acid comprising the nucleotide sequence of SEQ ID NO:2, SEQ ID NO:3, or the nucleotide sequence of the DNA insert of the plasmid deposited with ATCC as Accession Number PTA-1642; and
  (3) a polypeptide comprising at least 100 contiguous amino acids of the sequence set forth in SEQ ID NO:1.

14. The method of claim 13 wherein the polypeptide comprises an amino acid sequence which is at least 95% identical to the amino acid sequence of SEQ ID NO:1.

15. The method of claim 13 wherein the polypeptide is encoded by a nucleic acid molecule comprising a nucleotide sequence which is at least 90% identical to a nucleic acid comprising the nucleotide sequence of SEQ ID NO:2, SEQ ID NO:3, or the nucleotide sequence of the DNA insert of the plasmid deposited with ATCC as Accession Number PTA-1642.

16. The method of claim 13 wherein the polypeptide comprises at least 100 contiguous amino acids of the sequence set forth in SEQ ID NO:1.

17. The method of claim 13 wherein the polypeptide comprises the amino acid sequence of SEQ ID NO:1.

18. The method of claim 13 wherein the polypeptide is encoded by a nucleic acid molecule comprising the nucleotide sequence of SEQ ID NO:2.

19. The method of claim 13 wherein the polypeptide is encoded by a nucleic acid molecule comprising the nucleotide sequence of SEQ ID NO:3.

20. The method of claim 13 wherein the polypeptide is encoded by a nucleic acid molecule comprising the nucleotide sequence of the DNA insert of the plasmid deposited with ATCC as Accession Number PTA-1642.

21. The method of claim 13 wherein the polypeptide further comprises heterologous amino acid sequences.

* * * * *